Figure 1:
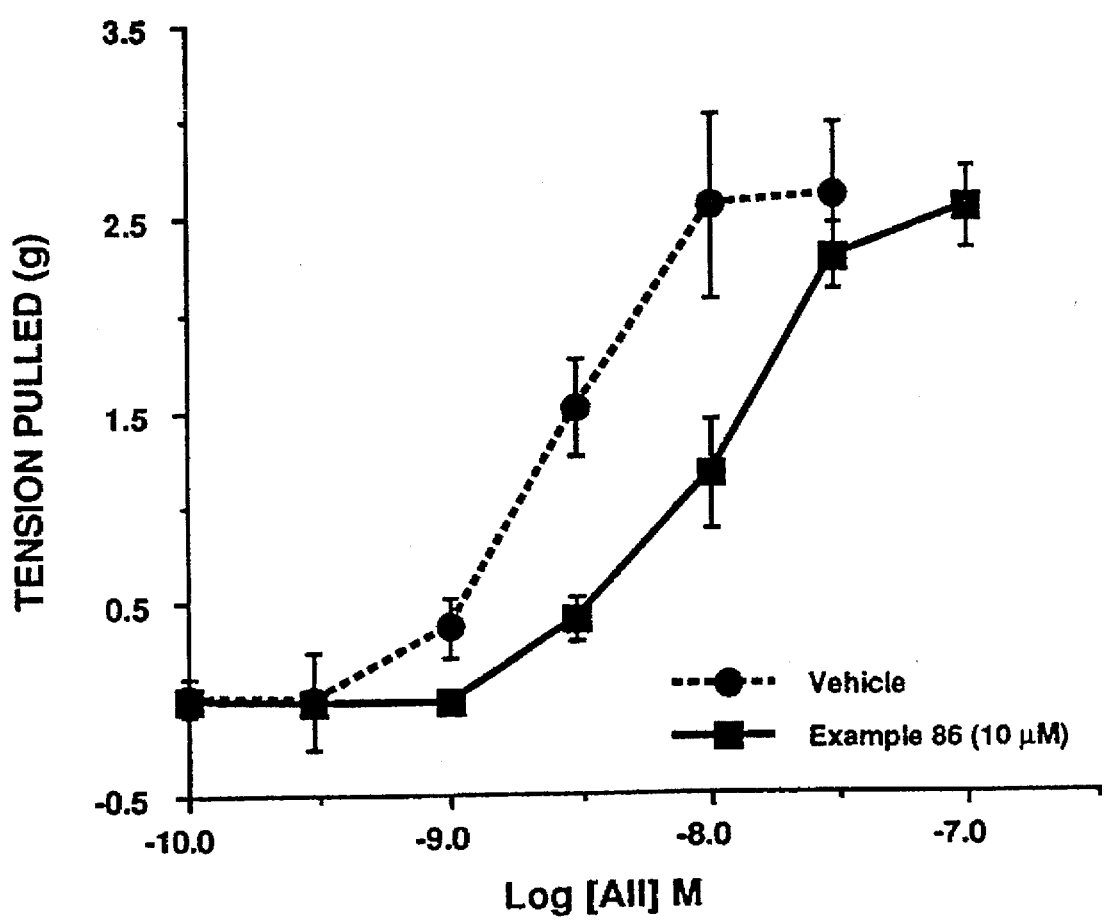

United States Patent [19]
Bowles et al.

[11] Patent Number: 5,741,794
[45] Date of Patent: Apr. 21, 1998

[54] HETEROCYCLIC SULFONAMIDE DERIVATIVES AS ANTAGONISTS OF PAF AND ANGIOTENSIN II

[75] Inventors: Stephen Arthur Bowles; Christopher David Floyd; Andrew Miller; Mark Whittaker; Lars Michael Wood, all of Oxford, United Kingdom

[73] Assignee: British Biotech Pharmaceuticals Limited, Cowley, England

[21] Appl. No.: 256,139

[22] PCT Filed: Jan. 6, 1993

[86] PCT No.: PCT/GB93/00010

§ 371 Date: Sep. 1, 1994

§ 102(e) Date: Sep. 1, 1994

[87] PCT Pub. No.: WO93/14069

PCT Pub. Date: Jul. 22, 1993

[30] Foreign Application Priority Data

Jan. 7, 1992 [GB] United Kingdom .................. 9200209

[51] Int. Cl.$^6$ ............... A61K 31/435; A61K 31/505; C07D 471/04; C07D 403/02
[52] U.S. Cl. ............ 514/261; 514/262; 514/303; 514/398; 514/399; 514/602; 544/264; 544/265; 546/118; 546/14; 548/339.1; 548/339.5; 548/342.1; 548/342.5; 548/343.1; 564/85; 564/88; 564/92; 564/93
[58] Field of Search ............... 514/261, 262, 514/303, 398, 399, 602; 544/264, 265; 546/118, 14; 548/339.1, 339.5, 342.1, 342.5, 343.1; 564/85, 88, 92, 93

[56] References Cited

U.S. PATENT DOCUMENTS 5,180,723  1/1993  Whittaker et al. ............... 546/118

FOREIGN PATENT DOCUMENTS 0144804   6/1985  European Pat. Off. .
WO 9203422  3/1992  WIPO .
WO9203423  3/1992  WIPO .

OTHER PUBLICATIONS

John V. Duncia, et al., Three Synthetic Routes to a Sterically Hindered Tetrazole. A New One-Step Mild Conversion of an Amide into a Tetrazole., J. Org. Chem., 56, pp. 2395–2400 (1991).

Primary Examiner—Matthew V. Grumbling
Attorney, Agent, or Firm—Hale and Dorr LLP

[57] ABSTRACT

Compounds of formula (I), wherein: A represents: a) a —VR$^6$ group wherein v is —C(=O), —C(=O)O—, —CH$_2$O—, —CH$_2$OC(=O)—, —C(=S)—, —CH$_2$OC (=O)NH—, —C(=S)O—, —CH$_2$S—, —C(=O) NHSO$_2$—, —SO$_2$NHC(=O)— or —CH$_2$OSiPh$_2$—; b) a —CH$_2$NR$^9$R$^{10}$ group or a —CONR$^9$R$^{10}$ group wherein each of R$^9$ and R$^{10}$ is independently hydrogen, -alkyl-, -alkenyl-, -alkynyl, -cycloalkyl, -cycloalkenyl, pyridyl (any of which may optionally be substituted) or a group —D as defined above or R$^9$ and R$^{10}$ together with the nitrogen atom to which they are attached form a nitrogen-containing heterocyclic ring; c) a group Y where Y is a 5- or 6-membered optionally substituted heterocyclic ring containing one or more heteroatoms selected from nitrogen, oxygen and sulphur; or d) a group —CH$_2$Y or —C(=O)NHY; where Y is as defined above; B represents a 5- or 6-membered heterocyclic ring containing one or more nitrogen atoms in its ring, are antagonists of platelet activating factor (PAF) and/or antagonists of angiotensin II.

15 Claims, 1 Drawing Sheet

HETEROCYCLIC SULFONAMIDE DERIVATIVES AS ANTAGONISTS OF PAF AND ANGIOTENSIN II

This invention relates primarily to novel substituted amino acid derivatives that possess pharmaceutical activity as antagonists of PAF and/or as antagonists of angiotensin II.

Platelet activating factor (PAF) is a bioactive phospholipid which has been identified as 1-O-hexadecyl/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, and cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds which have been disclosed as possessing activity as PAF antagonists include compounds which are structurally related to the PAF molecule such as glycerol derivatives (EP-A-0238202), and heterocyclic compounds such as 2,5-diaryl tetrahydrofurans (EP-A-0144804) and imidazopyridine derivatives (EP-A-0260613 and WO-A-8908653).

Angiotensin II is a bioactive octapeptide which is formed from angiotensin I by the action of angiotensin converting-enzyme. Angiotensin II is a powerful vasopressor agent which has been implicated as a causative agent of high blood pressure in various mammalian species, such as the rat, dog and man. Angiotensin II elevates blood pressure via binding to specific angiotensin II receptors on cell membranes. Thus the compounds of the invention, by virtue of their ability to antagonise the actions of angiotensin II, should be of value in the treatment of elevated blood pressure and congestive heart failure, glaucoma and intraocular hypertension, cognitive dysfunction, psoriasis and any other conditions in which angiotensin II is implicated.

Compounds which have been disclosed as possessing activity as angiotensin II antagonists include compounds which are structurally related to the angiotensin II peptide, but the experimental and clinical applications of these compounds have been limited by partial agonist activity (M. A. Ondetti and D. W. Cushman, *Annual Reports in Medicinal Chemistry*, 1978, 13, 82–91). Recently, several non-peptide compounds have been described as angiotensin II antagonists. Illustrative of such compounds are heterocyclic substituted biphenyl derivatives (D. J. Carini et al., *J. Med. Chem.*, 1991, 34, 2525–2547; P. R. Bovy et al., *Med. Chem. Res.*, 1991, 1, 86–94) and heterocyclic substituted benzofurans (EP-A-434,249).

The present invention provides novel and useful substituted sulphonyl amino acid derivatives and their pharmaceutically acceptable acid addition salts, and pharmaceutical uses thereof as PAF antagonists and angiotensin II antagonists.

According to a first aspect of the invention there is provided a compound of general formula I;

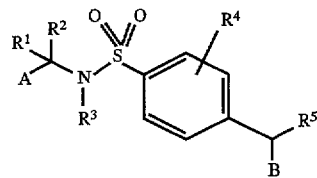

wherein:

A represents:

a) a $-VR^6$ group wherein V is $-C(=O)-$, $-C(=O)O-$, $-CH_2O-$, $-CH_2OC(=O)-$, $-C(=S)-$, $-CH_2OC(=O)NH-$, $-C(=S)O-$, $-CH_2S-$, $-C(=O)NHSO_2-$, $-SO_2NHC(=O)-$ or $-CH_2OSiPh_2-$; and R6 is hydrogen, $-C_1-C_{18}$ alkyl, $-C_2-C_{18}$ alkenyl, $-C_2-C_{18}$ alkynyl, $-(C_1-C_6$ alkyl$)OC_1-C_6$ alkyl, $-(C_1-C_6$ alkyl$)SC_1-C_6$ alkyl, $-(C_1-C_6$ alkyl$)O(C_1-C_6$ alkyl$)OC_1-C_6$ alkyl, $-C_3-C_8$ cycloalkyl, $-C_4-C_8$ cycloalkenyl or pyridyl, (any of which may optionally be substituted with one or more substituents selected from halogen, hydroxyl, nitro, nitrile or carboxyl), $C_1-C_4$ perfluoroalkyl, a group $-D$ or a $-(C_1-C_6$ alkyl$)OD$ group wherein D represents a group

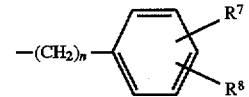

wherein n is an integer from 0 to 3, and each of $R^7$ and $R^8$ is independently hydrogen, $-C_1-C_6$ alkyl, $-C_2-C_6$ alkenyl, $-C_2-C_6$ alkynyl, halogen, $-CN$, $-CO_2H$, $-CO_2C_1-C_6$ alkyl, $-CONH_2$, $-CONHC_1-C_6$ alkyl, $-CON(C_1-C_6$ alkyl$)_2$, $-CHO$, $-CH_2OH$, $-CF_3$, $-OC_1-C_6$ alkyl, $-SC_1-C_6$ alkyl, $-SOC_1-C_6$ alkyl, $-SO_2C_1-C_6$ alkyl, $-NH_2$ or $-NHCOMe$;

or a group $-CH_2OSi(R^6)_3$ wherein $R^6$ is as defined above;

b) a $-CH_2NR^9R^{10}$ group or a $-CONR^9R^{10}$ group wherein each of $R^9$ and $R^{10}$ is independently hydrogen, $-C_1-C_{18}$ alkyl, $-C_2-C_{18}$ alkenyl, $-C_2-C_{18}$ alkynyl, $-C_3-C_8$ cycloalkyl, $-C_4-C_8$ cycloalkenyl, pyridyl (any of which may optionally be substituted with one or more substituents selected from halogen, hydroxyl, nitro, nitrile or carboxyl) or a group $-D$ as defined above or $R^9$ and $R^{10}$ together with the nitrogen atom to which they are attached form a 5 to 8 membered nitrogen-containing heterocyclic ring;

c) a group Y where Y is a 5- or 6-membered heterocyclic ring containing one or more heteroatoms selected from nitrogen, oxygen and sulphur and the ring may be optionally substituted with one or more substituents selected from $-C_1-C_6$ alkyl, $-OC_1-C_6$ alkoxy, halogen, $-CF_3$ and $-CN$; or d) a group $-CH_2-Y$ or $-C(=O)NHY$; where Y is as defined above;

$R^1$ and $R^2$ each independently represent hydrogen, halogen, $-C_1-C_6$ alkyl optionally substituted by one or more halogen atoms, $-C_2-C_6$ alkenyl, $-C_2-C_6$ alkynyl, $-(C_1-C_6$ alkyl$)CO_2C_1-C_6$ alkyl, $-(C_1-C_6$ alkyl$)SC_1-C_6$ alkyl, $-(C_1-C_6$ alkyl$)OC_1-C_6$ alkyl, $-(C_1-C_6$ alkyl$)N(C_1-C_6$ alkyl$)_2$, $-C_3-C_8$ cycloalkyl, $-C_4-C_8$ cycloalkenyl, $-(C_1-C_6$ alkyl$)C_3-C_8$ cycloalkyl, $-(C_1-C_6$ alkyl$)C_4-C_8$ cycloalkenyl, $-(C_1-C_6$ alkyl$)OC_3-C_8$ cycloalkyl, —($C_1$–$C_6$ alkyl)O$C_4$–$C_8$ cycloalkenyl, —($C_1$–$C_6$ alkyl)S$C_3$–$C_8$ cycloalkyl, —($C_1$–$C_6$ alkyl)S$C_4$–$C_8$ cycloalkenyl, a side chain of a naturally occurring amino acid, a group —D, or a —($C_1$–$C_6$ alkyl)OD group wherein D is as defined above;

or $R^1$ and $R^2$ together with the carbon atom to which they are attached form a $C_3$–$C_8$ cycloalkyl ring;

$R^3$ represents hydrogen, —$C_1$–$C_6$ alkyl, —$C_2$–$C_6$ alkenyl, —$C_2$–$C_6$ alkynyl, —CO$C_1$–$C_6$ alkyl, —CO$_2$$C_1$–$C_6$ alkyl, —(CO$C_1$–$C_6$ alkyl)phenyl, —(CO$_2$$C_1$–$C_6$ alkyl)phenyl, —($C_1$–$C_6$ alkyl)O$C_1$–$C_6$ alkyl, —($C_1$–$C_6$ alkyl)S$C_1$–$C_6$ alkyl, —($C_1$–$C_6$ alkyl)CO$_2$$C_1$–$C_6$ alkyl, —$C_3$–$C_8$ cycloalkyl, —$C_4$–$C_8$ cycloalkenyl or a group —D wherein D is as defined above;

or $R^1$ together with $R^3$ and the atoms to which they are attached form a 5 to 8 membered nitrogen-containing heterocyclic ring;

$R^4$ represents hydrogen, —$C_1$–$C_6$ alkyl, —$C_2$–$C_6$ alkenyl, halogen, —O$C_1$–$C_6$ alkyl, —$C_1$–$C_4$ perfluoroalkyl or —$C_3$–$C_8$ cycloalkyl;

$R^5$ represents hydrogen, —$C_1$–$C_6$ alkyl, —$C_2$–$C_6$ alkenyl, —$C_2$–$C_6$ alkynyl, —CO$_2$$C_1$–$C_6$ alkyl, —S$C_1$–$C_6$ alkyl, —($C_1$–$C_6$ alkyl)S$C_1$–$C_6$ alkyl, —($C_1$–$C_6$ alkyl)O$C_1$–$C_6$ alkyl, —($C_1$–$C_6$ alkyl) phenyl or thiophenyl;

B represents a 5- or 6-membered heterocyclic ring containing one or more nonquaternised nitrogen atoms in its ring, which heterocyclic ring may be optionally fused to a benzene ring or to a further 5-, 6- or 7-membered heterocyclic ring containing one or more nitrogen atoms, wherein at least one of the said heterocyclic rings may also contain an oxygen or sulphur atom, and wherein any of the rings may be optionally substituted with one or more substituents selected from hydrogen, halogen, —$C_1$–$C_4$ perfluoroalkyl, hydroxyl, carbonyl, thiocarbonyl, formyl, carboxyl, —CONH$_2$, —NO$_2$, a group —D wherein D is as defined above, —$R^{11}$, —O$R^{11}$, —S$R^{11}$, —SO$R^{11}$, —SO$_2$$R^{11}$, —NH$R^{11}$, —N$R^{11}$$R^{11}$, —CO$_2$$R^{11}$ or —CONH$R^{11}$ wherein $R^{11}$ is —$C_1$–$C_6$ alkyl, —$C_2$–$C_6$ alkenyl, —$C_2$–$C_6$ alkynyl, —$C_3$–$C_8$ cycloalkyl or $C_4$–$C_8$ cycloalkenyl each of which is optionally substituted with one or more substituents selected from halogen, hydroxyl, amino, carboxyl, —$C_1$–$C_4$ perfluoroalkyl, —$C_1$–$C_6$ alkyl, —$C_2$–$C_6$ alkenyl, —$C_2$–$C_6$ alkynyl, —$C_3$–$C_8$ cycloalkyl, —$C_4$–$C_8$ cycloalkenyl, —O$C_1$–$C_6$ alkyl, —S$C_1$–$C_6$ alkyl, tetrazol-5-yl, a group —D wherein D is as defined above or a heteroaryl or heteroarylmethyl group;

provided that B is other than a substituted or unsubstituted 1H-benzimidazoyl, 1-H-imidazo[4,5-c]pyridyl, 3-H-imidazo[4,5-c]pyridyl or 5-H-imidazo[4,5-c]pyridyl derivative;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "$C_1$–$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_1$–$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl and octadecyl. From one to six carbon atoms may be preferred.

As used herein the term "$C_2$–$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_2$–$C_{18}$ alkenyl" refers to straight chain or branched chain hydrocarbon groups having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl, and farnesyl. From two to six carbon atoms may be preferred.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "$C_2$–$C_{18}$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

As used herein, the term "$C_1$–$C_4$ perfluoroalkyl" refers to straight chain or branched chain groups having from one to four carbon atoms and substituted by more than one fluorine atom. This term would include for example, trifluoromethyl, 2,2,2-trifluoroethyl, pentafluoroethyl, 3,3,3-trifluoro-n-propyl, septafluoro-i-propyl, septafluoro-n-propyl, septafluoro-i-propyl, 4,4,4-trifluoro-n-butyl, nonafluoro-n-butyl, nonafluoro-sec-butyl and nonafluoro-i-butyl.

As used herein the term "O$C_1$–$C_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "S$C_1$–$C_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$–$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. The amino acid side chains may be protected; for example the carboxyl groups of aspartic acid, glutamic acid and α-aminoadipic acid may be esterified (for example as a $C_1$-$C_6$ alkyl ester), the amino groups of lysine, ornithine, 5-hydroxylysine, 4-hydroxyproline may be converted to amides (for example as a $COC_1$-$C_6$ alkyl amide) or carbamates (for example as a $C(=O)OC_1$-$C_6$ alkyl or $C(=O)OCH_2Ph$ carbamate), the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a $C_1$-$C_6$ alkyl or a ($C_1$-$C_6$ alkyl)phenyl ether) or esters (for example a $C(=O)C_1$-$C_6$ alkyl ester) and the thiol group of cysteine may be converted to thioethers (for example a $C_1$-$C_6$ alkyl thioether) or thioesters (for example a $C(=O)C_1$-$C_6$ alkyl thioester). The stereochemistry at the carbon atom to which the amino acid side chain is attached may be either D or L.

As used herein, the term "nitrogen-containing heterocyclic ring" refers to an aromatic or alicyclic ring comprising one or more nitrogen atoms and optionally one or more other heteroatoms. Illustrative of such rings are pyrrolidine, piperidine, hexamethyleneimine, heptamethyleneimine, morpholine and piperazine.

As used herein, the term "heteroaryl" refers to a 5- or 6-membered substituted or unsubstituted aromatic heterocycle containing one or more heteroatoms. Illustrative of such rings are thienyl, furyl, imidazolyl, oxadiazolyl, pyridyl, pyrazinyl each of which may be optionally substituted by methyl or methoxy.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

It is considered that the main structural features of compounds of general formula I that are particularly significant in providing their PAF antagonist activity, are the nitrogen heterocycle (B group) and the subunit

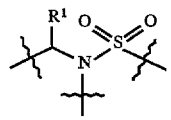
(i)

Since it is the presence of the B group and the subunit (i) that appear to be crucial for retention of PAF antagonist activity, there may be considerable variation of the substituent groups $R^3$, and A without loss of such activity. Any of the the wide range of substituents $R^3$ and A defined above may be used with retention of PAF antagonist activity.

The linkage

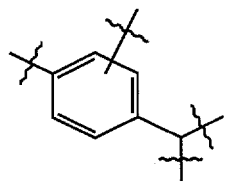
(ii)

is considered to function as a spacer element, separating the nitrogen heterocycle from the amino acid subunit. The nature or identity of the substituents $R^4$ and $R^5$ therefore is not thought to be particularly critical and any of the wide range of substituents $R^4$ and $R^5$ specified above may be used with retention of PAF antagonist activity.

It is considered that the main structural features of compounds of general formula I that are particularly significant in providing their angiotensin II antagonist activity, are the A group and the B group. The A group is preferably a carboxylic acid or any one of the groups claimed above for A that may serve as an acidic isostere (for example tetrazolyl). The group B is the nitrogen heterocycle and an important requirement for angiotensin II activity is that this heterocycle should possess at least one —$C_1$-$C_6$ alkyl group, which is important for providing a lipophilic interaction with the angiotensin II receptor. It is understood that other substituents of the group B from the wide range specified above may enhance angiotensin II activity. The unit

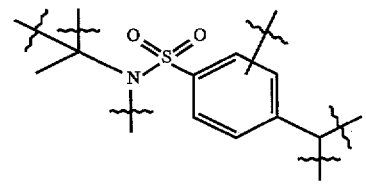
(iii)

is considered to function as a spacer element, providing an optimal spacial orientation of the B group with respect to the A group. The nature or identity of the substituents $R^1$, $R^2$, $R^3$, $R^4$ and $R^5$ therefore is not thought to be particularly critical and any of the wide range of substituents $R^1$, $R^2$, $R^3$, $R^4$ and $R^5$ specified above may be used with retention of angiotensin ISI antagonist activity. Although not claimed here variations of the unit (iii) that involve replacement of the 1,4-phenylene group with disubstituted alicyclic, cyclic and heterocyclic moieties are considered likely to result in compounds that also possess angiotensin II antagonist activity.

Preferred compounds include those in which, independently or in any compatible combination:
A represents a $VR^6$ group wherein V is a —C(=O)O—, —$CH_2O$—, —$CH_2OSiPh_2$— or —C(=O)$NHSO_2$— group and $R^6$ represents a hydrogen atom, a —$C_1$-$C_6$ alkyl (for example methyl, ethyl, propyl or t-butyl) group or a —$C_1$-$C_4$ perfluoroalkyl (for example trifluoromethyl) group, or A represents a Y group or a —C(=O)NHY group where Y represents a tetrazolyl group;

$R^1$ represents a hydrogen atom, a —$C_1$-$C_6$ alkyl (for example methyl, isopropyl, n-butyl, isobutyl or 2-methylpropyl) group, a —($C_1$-$C_6$ alkyl)$CO_2C_1$-$C_6$ alkyl (for example ethyl 3-propionate) group, a —($C_1$-$C_6$ alkyl)$SC_1$-$C_6$ alkyl (for example methylthioethylene) group, the side chain of a naturally occurring amino acid, a group —D or a —($C_1$-$C_6$ alkyl)OD group;

$R^2$ represents a hydrogen atom or a —$C_1$-$C_6$ alkyl (for example methyl) group, or together with $R^1$ and the carbon atom to which they are attached forms a $C_3$–$C_8$ cycloalkyl (for example cyclohexyl) ring;

$R^3$ represents a hydrogen atom or a —$C_1$–$C_6$ alkyl (for example methyl, ethyl or propyl) group;

$R^4$ represents a hydrogen atom;

$R^5$ represents a hydrogen atom;

n represents an integer of 0 or 1;

$R^7$ represents a hydrogen atom or a —$OC_1$–$C_6$ alkyl (for example methoxy) group;

$R^8$ represents a hydrogen atom;

B represents a 5- or 6-membered heterocyclic ring selected from pyrrolyl, imidazolyl, pyrazolyl, triazolyl, tetrazolyl, thiazolyl, oxazolyl, pyridyl, pyrimidyl, pyrazinyl or pyridazinyl which heterocyclic ring may be optionally fused to a benzene ring or to a further 5-, 6- or 7-membered heterocyclic ring selected from furan, thiophene, pyrrole, imidazole, pyrazole, triazole, tetrazole, thiazole, oxazole, pyridine, pyrimidine, pyrazine, pyridiazine, triazine, azepine, oxazepine, diazepine or thiazepine, wherein any of the rings may optionally be substituted with substituents selected from hydrogen, halogen, —$C_1$–$C_4$ perfluoroalkyl, hydroxyl, carbonyl, thiocarbonyl, formyl, carboxyl, —$CONH_2$, —$NO_2$, a group —D wherein D is as defined above, —$R^{11}$, —$OR^{11}$, —$SR^{11}$, —$SOR^{11}$, $SO_2R^{11}$, —$NH_2R^{11}$, —$NR^{11}R^{11}.CO_2R^{11}$ or $CONHR^{11}$ wherein $R^{11}$ is —$C_1$–$C_6$ alkyl, —$C_2$–$C_6$ alkenyl, —$C_2$–$C_6$ alkynyl, —$C_3$–$C_8$ cycloalkyl or —$C_4$–$C_8$ cycloalkenyl, each of which is optionally substituted with one or more substituents selected from halogen, hydroxyl, amino, carboxyl, —$C_1$–$C_4$ perfluoroalkyl, —$C_1$–$C_6$ alkyl, —$C_2$–$C_6$ alkenyl, —$C_2$–$C_6$ alkynyl, —$C_3$–$C_8$ cycloalkyl, —$C_4$–$C_8$ cycloalkenyl, —$OC_1$–$C_6$ alkyl, —$SC_1$–$C_6$ alkyl, tetrazol-5-yl, a group —D wherein D is as defined above or a heteroaryl or heteroarylmethyl group;

provided that B is other than a substituted or unsubstituted 1H-benzimidazoyl, 1-H-imidazo[4,5-c]pyridyl, 3-H-imidazo[4,5-c]pyridyl or 5-H-imidazo[4,5-c]pyridyl derivative.

Particularly preferred compounds are those in which B represents an imidazolyl (for example 1-H-imidazolyl, 1-H-2-methylimidazolyl, 1-H-2-nitroimidazolyl, 1-H-2-phenylimidazolyl, 1-H-2,4-dimethylimidazolyl, 1-H-2,5-dimethylimidazolyl, 1-H-4,5-diphenylimidazolyl, 1-H-2-n-butyl-4-chloro-5-hydroxymethylimidazolyl, 1H-2-n-propyl-4-chloro-5-formylimidazolylmethyl, 1H-2on-butyl-4-trifluoromethyl-5-hydroxycarbonylimidazolyl or 1H-2-n-butyl-4-chloro-5-(3-methyl-1,2,4-oxadiazol-5-yl) imidazolyl) group, a imidazo[4,5-b]pyridyl (for example 1H-imidazo[4,5-b]pyridyl, 3H-imidazo[4,5-b]pyridyl or 3H-2-ethyl-5,7-dimethylimidazo[4,5-b]pyridinyl) group, a purinyl (for example 9H-2,6-dichloropurinyl or 7H-8-n-butyl-3,7-dihydro-1,3-dimethylpurine-2,6-dionyl) group, a 3,7-dihydropurine-2,6-dionyl (for example 1H-8-n-butyl-3,7-dihydro-1,3-dimethylpurine-2,6-dionyl) group, a pyrrolo[2,3-b]pyridinyl (for example 1H-2-n-propylpyrrolo[2,3-b]pyridinyl) group, a pyrrolo[3,2-c]pyridinyl (for example 1H-4-chloro-2,6-dimethylpyrrolo[3,2-c]pyridinyl), a pyrrolo[2,3-d]pyrimidin-6-onyl (for example 7H-2,4-dimethyl-5,7-dihydropyrrolo[2,3-d]pyrimidin-6-onyl) group, a isoquinol-1-onyl (for example 2H-3-n-propylisoquinol-1-onyl) group, a thieno[2,3-d]pyrimidin-4-onyl (for example 3H-2-n-butyl-5-methylthieno[2,3-d]pyrimidin-4-onyl) group, a imidazo[1,2-b]-1,2,4-triazolyl (for example 3H-2-n-butyl-6-methyl-5-phenylimidazo[1,2-b]-1,2,4-triazolyl or 4H-3on-butyl-5-(4-chlorobenzylthio)-1,2,4-triazolyl) group, a 1,2,4-triazolyl (for example 1H-3,5-dibutyl-1,2,4-triazolyl) group, a quinazolin-4-onyl (for example 3H-2-n-butyl-6-(1-hydroxy-1-methylethyl) quinazolin-4-onyl) group, a 1,2,4-benzothiadiazinedioxide (for example 4H-3-ethylthio-1,2,4-benzothiadiazinedioxide) group, a 1,6-dihydropyrimidinyl (for example 1H-2-n-butyl-4-chloro-1,6-dihydro-5-hydroxycarbonyl-6-methyl-pyrimidinyl) group, a pyrimidin-4-onyl (for example 3H-2-ethylpyrimidin-4-onyl) group, a pyrrolyl (for example 1H-2-n-propylpyrrolyl) group, a pyrido[2,3-d]pyrimidin-4-onyl (for example 3H-2-n-butyl-6-methylpyrido[2,3-d] pyrimidin-4-onyl) group, a 1,4-dihydo-4-thioxoquinolinyl (for example 1H-3-n-butyl-1,4-dihydo-4-thioxoquinolinyl) group, or a 4-spirocyclopentane-2-imidazoline-5-onyl (for example 1H-2-n-butyl-4-spirocyclopentane-2-imidazoline-5-onyl) group.

For PAF receptor antagonist activity $R^1$ preferably represents the side chain of the amino acid leucine and $R^2$ is a hydrogen atom.

For angiotensin II receptor antagonist activity A preferably represents a —C(=O)OH group, a —C(=O) $NHSO_2C_1$–$C_6$ alkyl group, a —C(=O)$NHSO_2C_1$–$C_4$ perfluoroalkyl group, a tetrazolyl group or a —C(=O) NHtetrazolyl group.

Exemplary compounds include:

1. N-4-(1H-2-Phenylimidazolylmethyl)phenylsulphonyl-L-leucine ethyl ester,
2. N-Methyl-N-4-(1H-2-nitroimidazolylmethyl) phenylsulphonyl-L-leucine ethyl ester,
3. N-4-(1H-4,5-Diphenylimidazolylmethyl) phenylsulphonyl-L-leucinyl ethyl ether,
4. N-4-(1H-2-Butyl-4-chloro-5-hydroxymethylimidazolylmethyl)phenylsulphonyl-L-leucine ethyl ester,
5. N-4-(1H-2-Butyl-4-chloro-5-hydroxymethylimidazolylmethyl) phenylsulphonylglycine methyl ester,
6. N-4-(1H-2-Butyl-4-chloro-5-hydroxymethylimidazolylmethyl)phenylsulphonyl-2,2-dimethylglycine methyl ester,
7. N-4-(1H-2-Butyl-4-chloro-5-hydroxymethylimidazolylmethyl)phenylsulphonyl-1-methoxycarbonylcyclohexylamine,
8. N-4-(1H-2-Butyl-4-chloro-5-hydroxymethylimidazolylmethyl)phenylsulphonyl-D,L-alanine methyl ester,
9. N-4-(1H-2-Butyl-4-chloro-5-hydroxymethylimidazolylmethyl)phenylsulphonyl-D-phenylalanine methyl ester,
10. N-4-(1H-2-Butyl-4-chloro-5-hydroxymethylimidazolylmethyl)phenylsulphonyl-L-phenylalanine methyl ester,
1. N-4-(1H-2-Butyl-4-chloro-5-hydroxymethylimidazolylmethyl)phenylsulphonyl-L-valine methyl ester,
12. N-4-(1H-2-Butyl-4-chloro-5-hydroxymethylimidazolylmethyl)phenylsulphonyl-D-valine methyl ester,
13. N-4-(1H-2-Butyl-4-chloro-5-hydroxymethylimidazolylmethyl)phenylsulphonyl-D,L-t-butylglycine methyl ester,
14. N-4-(1H-2-Butyl-4-chloro-5-hydroxymethylimidazolylmethyl)phenylsulphonyl-D-leucine ethyl ester,
15. N-4-(1H-2-Butyl-4-chloro-5-hydroxymethylimidazolylmethyl)phenylsulphonyl-L-isoleucine ethyl ester.

16. N-4-(1H-2-Butyl-4-chloro-5-hydroxymethylimidazolylmethyl)phenylsulphonyl-D-isoleucine ethyl ester,
17. N-4-(1H-2-Butyl-4-chloro-5-hydroxymethylimidazolylmethyl)phenylsulphonyl-D,L-norleucine ethyl ester,
18. N-4-(1H-2-Butyl-4-chloro-5-hydroxymethylimidazolylmethyl)phenylsulphonyl-O-methyl-L-tyrosine methyl ester,
19. N-4-(1H-2-Butyl-4-chloro-5-hydroxymethylimidazolylmethyl)phenylsulphonyl-O-methyl-D-tyrosine methyl ester,
20. N-4-(1H-2-Butyl-4-chloro-5-hydroxymethylimidazolylmethyl)phenylsulphonyl-O-benzyl-D,L-serine methyl ester,
21. N-4-(1H-2-Butyl-4-chloro-5-hydroxymethylimidazolylmethyl)phenylsulphonyl-D,L-methionine methyl ester,
22. N-4-(1H-2-Butyl-4-chloro-5-hydroxymethylimidazolylmethyl)phenylsulphonyl-D,L-aspartic acid diethyl ester,
23. N-Methyl-N-4-(1H-2-butyl-4-chloro-5-hydroxymethylimidazolylmethyl)phenylsulphonyl-L-leucine ethyl ester,
24. N-Methyl-N-4-(1H-2-butyl-4-chloro-5-hydroxymethylimidazolylmethyl)phenylsulphonyl-L-leucine n-propyl ester,
25. N-Methyl-N-4-(1H-2-butyl-4-chloro-5-hydroxymethylimidazolylmethyl)phenylsulphonylglycine methyl ester,
26. N-Methyl-N-4-(1H-2-butyl-4-chloro-5-hydroxymethylimidazolylmethyl)phenylsulphonyl-2,2-dimethylglycine methyl ester,
27. N-Methyl-N-4-(1H-2-butyl-4-chloro-5-hydroxymethylimidazolylmethyl)phenylsulphonyl-1-methoxycarbonylcyclohexylamine,
28. N-Methyl-N-4-(1H-2-butyl-4-chloro-5-hydroxymethylimidazolylmethyl)phenylsulphonyl-D,L-alanine methyl ester,
29. N-Ethyl-N-4-(1H-2-butyl-4-chloro-5-hydroxymethylimidazolylmethyl)phenylsulphonyl-D-phenylalanine methyl ester,
30. N-Ethyl-N-4-(1H-2-butyl-4-chloro-5-hydroxymethylimidazolylmethyl)phenylsulphonyl-L-phenylalanine methyl ester,
31. N-Methyl-N-4-(1H-2-butyl-4-chloro-5-hydroxymethylimidazolylmethyl)phenylsulphonyl-L-valine methyl ester,
32. N-Methyl-N-4-(1H-2-butyl-4-chloro-5-hydroxymethylimidazolylmethyl)phenylsulphonyl-D-valine methyl ester,
33. N-Methyl-N-4-(1H-2-butyl-4-chloro-5-hydroxymethylimidazolylmethyl)phenylsulphonyl-D,L-t-butylglycine methyl ester,
34. N-Methyl-N-4-(1H-2-butyl-4-chloro-5-hydroxymethylimidazolylmethyl)phenylsulphonyl-D-leucine ethyl ester,
35. N-n-Propyl-N-4-(1H-2-butyl-4-chloro-5-hydroxymethylimidazolylmethyl)phenylsulphonyl-L-isoleucine ethyl ester,
36. N-n-Propyl-N-4-(1H-2-butyl-4-chloro-5-hydroxymethylimidazolylmethyl)phenylsulphonyl-D-isoleucine ethyl ester,
37. N-Methyl-N-4-(1H-2-butyl-4-chloro-5-hydroxymethylimidazolylmethyl)phenylsulphonyl-D,L-norleucine ethyl ester,
38. N-Methyl-N-4-(1H-2-butyl-4-chloro-5-hydroxymethylimidazolylmethyl)phenylsulphonyl-O-methyl-L-tyrosine methyl ester,
39. N-Methyl-N-4-(1H-2-butyl-4-chloro-5-hydroxymethylimidazolylmethyl)phenylsulphonyl-O-methyl-D-tyrosine methyl ester,
40. N-Methyl-N-4-(1H-2-butyl-4-chloro-5-hydroxymethylimidazolylmethyl)phenylsulphonyl-O-benzyl-D,L-serine methyl ester,
41. N-Methyl-N-4-(1H-2-butyl-4-chloro-5-hydroxymethylimidazolylmethyl)phenylsulphonyl-D,L-methionine methyl ester,
42. N-Methyl-N-4-(1H-2-butyl-4-chloro-5-hydroxymethylimidazolylmethyl)phenylsulphonyl-D,L-aspartic acid diethyl ester,
43. N-Methyl-N-4-(1H-2-ethylimidazolylmethyl)phenylsulphonyl-L-leucine methyl ester,
44. N-Methyl-N-4-(1H-2-n-propylimidazolylmethyl)phenylsulphonyl-L-leucine methyl ester,
45. (A) N-4-(3H-Imidazo[4,5-b]pyridylmethyl)phenylsulphonyl-L-leucinyl ethyl ether, (B) N-4-(1H-Imidazo[4,5-b]pyridylmethyl)phenylsulphonyl-L-leucinyl ethyl ether,
46. N-4-(1H-2-n-Propylpyrrolo[2,3-b]pyridinylmethyl)phenylsulphonylglycine methyl ester,
47. N-4-(2H-3-n-Propylisoquinol-1-onylmethyl)phenylsulphonyl-2,2-dimethylglycine methyl ester,
48. N-4-(3H-2-n-Butyl-5-methylthieno[2,3-d]pyrimidin-4-onylmethyl)phenylsulphonyl-1-methoxycarbonylcyclohexylamine, 49. N-4-(3H-2-n-Butyl-6-methyl-5-phenylimidazo[1,2-b]-1,2,4-triazolylmethyl)-phenylsulphonyl-D,L-alanine methyl ester,
50. N-4-(1H-4-Chloro-2,6-dimethylpyrrolo[3,2-c]pyridinylmethyl)phenylsulphonyl-L-phenylalanine methyl ester,
51. N-4-(1H-4-Chloro-2,6-dimethylpyrrolo[3,2-c]pyridinylmethyl)phenylsulphonyl-D-phenylalanine methyl ester,
52. N-4-(7H-8-n-Butyl-3,7-dihydro-1,3-dimethylpurine-2,6-dionylmethyl)phenylsulphonyl-L-phenylalanine methyl ester,
53. N-4-(7H-8-n-Butyl-3,7-dihydro-1,3-dimethylpurine-2,6-dionylmethyl)phenylsulphonyl-L-phenylalanine methyl ester,
54. N-4-(1H-3,5-Dibutyl-1,2,4-triazolylmethyl)phenylsulphonyl-L-valine methyl ester,
55. N-4-(1H-3,5-Dibutyl-1,2,4-triazolylmethyl)phenylsulphonyl-D-valine methyl ester,
56. N-4-(3H-2-n-Butyl-6-(1-hydroxy-1-methylethyl)quinazolin-4-onylmethyl)phenylsulphonyl-D,L-t-butylglycine methyl ester,
57. N-4-(7H-2,4-Dimethyl-5,7-dihydropyrrolo[2,3-d]pyrimidin-6-onylmethyl)phenylsulphonyl-L-leucine ethyl ester,
58. N-4-(7H-2,4-Dimethyl-5,7-dihydropyrrolo[2,3-d]pyrimidin-6-onylmethyl)phenylsulphonyl-D-leucine ethyl ester,
59. N-4-(1H-2-n-Propyl-4-chloro-5-formylimidazolylmethyl)phenylsulphonyl-L-isoleucine ethyl ester,
60. N-4-(1H-2-n-Propyl-4-chloro-5-formylimidazolylmethyl)phenylsulphonyl-D-isoleucine ethyl ester,
61. N-Methyl-N-4-(3H-2-ethyl-5,7-dimethylimidazo[4,5-b]pyridinylmethyl)phenylsulphonylglycine methyl ester,
62. N-Methyl-N-4-(3H-2-ethyl-5,7-dimethylimidazo[4,5-b]pyridinylmethyl)phenylsulphonyl-2,2-dimethylglycine methyl ester,
63. N-Methyl-N-4-(3H-2-ethyl-5,7-dimethylimidazo[4,5-b]pyridinylmethyl)phenylsulphonyl-1-methoxycarbonylcyclohexylamine, 64. N-Methyl-N-4-(3H-2-ethyl-5,7-dimethylimidazo[4,5-b]pyridinylmethyl)phenylsulphonyl-D,L-alanine methyl ester,
65. N-4-(3H-2-Ethyl-5,7-dimethylimidazo[4,5-b]pyridinylmethyl)phenylsulphonyl-D,L-alanine methyl ester,
66. N-Methyl-N-4-(3H-2-ethyl-5,7-dimethylimidazo[4,5-b]pyridinylmethyl)phenylsulphonyl-D,L-alanine methyl ester,
67. N-Methyl-N-4-(4H-3-ethylthio-1,2,4-benzothiadiazinedioxidemethyl)phenylsulphonyl-D-phenylalanine methyl ester,
68. N-Methyl-N-4-(4H-3-ethylthio-1,2,4-benzothiadiazinedioxidemethyl)phenylsulphonyl-L-phenylalanine methyl ester,
69. N-Methyl-N-4-(4H-3-n-butyl-5-(4-chlorobenzylthio)-1,2,4-triazolylmethyl)phenylsulphonyl-L-valine methyl ester,
70. N-Methyl-N-4-(4H-3-n-butyl-5-(4-chlorobenzylthio)-1,2,4-triazolylmethyl)phenylsulphonyl-D-valine methyl ester,
71. N-Methyl-N-4-(1H-2-n-butyl-4-chloro-1,6-dihydro-5-hydroxycarbonyl-6-methylpyrimidinylmethyl)phenylsulphonyl-D,L-t-butylglycine methyl ester,
72. N-Methyl-N-4-(1H-2-n-butyl-4-trifluoromethyl-5-hydroxycarbonylimidazolylmethyl)phenylsulphonyl-D-leucine ethyl ester,
73. N-Methyl-N-4-(1H-2-n-butyl-4-trifluoromethyl-5-hydroxycarbonylimidazolylmethyl)phenylsulphonyl-L-leucine ethyl ester,
74. N-Methyl-N-4-(3H-2-ethylpyrimidin-4-onylmethyl)phenylsulphonyl-L-isoleucine ethyl ester,
75. N-Methyl-N-4-(3H-2-ethylpyrimidin-4-onylmethyl)phenylsulphonyl-D-isoleucine ethyl ester,
76. N-Methyl-N-4-(1H-2-n-propylpyrrolylmethyl)phenylsulphonyl-D,L-norleucine ethyl ester,
77. N-Methyl-N-4-(3H-2-n-butyl-6-methylpyrido[2,3-d]pyrimidin-4-onylmethyl)phenylsulphonyl-O-methyl-L-tyrosine methyl ester,
78. N-Methyl-N-4-(3H-2-n-butyl-6-methylpyrido[2,3-d]pyrimidin-4-onylmethyl)phenylsulphonyl-O-methyl-D-tyrosine methyl ester,
79. N-Methyl-N-4-(1H-3-n-butyl-1,4-dihydo-4-thioxoquinolinylmethyl)phenylsulphonyl-O-benzyl-D,L-serine methyl ester,
80. N-Methyl-N-4-(1H-2-n-butyl-4-chloro-5-(3-methyl-1,2,4-oxadiazol-5-yl)imidazolylmethyl)-phenylsulphonyl-D,L-methionine methyl ester,
81. N-Methyl-N-4-(1H-2-n-butyl-4-spirocyclopentane-2-imidazoline-5-onylmethyl)phenylsulphonyl-D,L-aspartic acid diethyl ester,
82. N-Methyl-N-4-(9H-2,6-dichloropurinylmethyl)phenylsulphonyl-L-leucine n-propyl ester,
83. N-4-(1H-Imidazolylmethyl)phenylsulphonyl-L-leucinyl t-butyldiphenylsilyl ether,
84. N-4-(1H-Imidazolylmethyl)phenylsulphonyl-L-leucinol,
85. N-4-(1H-2-Methylimidazolylmethyl)phenylsulphonyl-L-leucinol,
86. N-Methyl-N-4-(1H-2-butyl-4-chloro-5-hydroxymethylimidazolylmethyl)phenylsulphonyl-L-leucine,
87. N-Methyl-N-4-(1H-2-ethylimidazolylmethyl)phenylsulphonyl-L-leucine,
88. N-Methyl-N-4-(1H-2-n-propylimidazolylmethyl)phenylsulphonyl-L-leucine,
89. N-4-(1H-2-Butyl-4-chloro-5-hydroxymethylimidazolylmethyl)phenylsulphonylglycine,
90. N-4-(1H-2-Butyl-4-chloro-5-hydroxymethylimidazolylmethyl)phenylsulphonyl-2,2-dimethylglycine,
91. N-4-(1H-2-Butyl-4-chloro-5-hydroxymethylimidazolylmethyl)phenylsulphonyl-1-aminocyclohexanecarboxylic acid,
92. N-4-(1H-2-Butyl-4-chloro-5-hydroxymethylimidazolylmethyl)phenylsulphonyl-D,L-alanine,
93. N-4-(1H-2-Butyl-4-chloro-5-hydroxymethylimidazolylmethyl)phenylsulphonyl-D-phenylalanine,
94. N-4-(1H-2-Butyl-4-chloro-5-hydroxymethylimidazolylmethyl)phenylsulphonyl-L-phenylalanine,
95. N-4-(1H-2-Butyl-4-chloro-5-hydroxymethylimidazolylmethyl)phenylsulphonyl-L-valine,
96. N-4-(1H-2-Butyl-4-chloro-5-hydroxymethylimidazolylmethyl)phenylsulphonyl-D-valine,
97. N-4-(1H-2-Butyl-4-chloro-5-hydroxymethylimidazolylmethyl)phenylsulphonyl-D,L-t-butylglycine,
98. N-4-(1H-2-Butyl-4-chloro-5-hydroxymethylimidazolylmethyl)phenylsulphonyl-D-leucine,
99. N-4-(1H-2-Butyl-4-chloro-5-hydroxymethylimidazolylmethyl)phenylsulphonyl-D-leucine,
100. N-4-(1H-2-Butyl-4-chloro-5-hydroxymethylimidazolylmethyl)phenylsulphonyl-L-isoleucine,
101. N-4-(1H-2-Butyl-4-chloro-5-hydroxymethylimidazolylmethyl)phenylsulphonyl-D-isoleucine,
102. N-4-(1H-2-Butyl-4-chloro-5-hydroxymethylimidazolylmethyl)phenylsulphonyl-D,L-norleucine,
103. N-4-(1H-2-Butyl-4-chloro-5-hydroxymethylimidazolylmethyl)phenylsulphonyl-O-methyl-L-tyrosine,
104. N-4-(1H-2-Butyl-4-chloro-5-hydroxymethylimidazolylmethyl)phenylsulphonyl-O-methyl-D-tyrosine,
105. N-4-(1H-2-Butyl-4-chloro-5-hydroxymethylimidazolylmethyl)phenylsulphonyl-O-benzyl-D,L-serine,
106. N-4-(1H-2-Butyl-4-chloro-5-hydroxymethylimidazolylmethyl)phenylsulphonyl-D,L-methionine,
107. N-4-(1H-2-Butyl-4-chloro-5-hydroxymethylimidazolylmethyl)phenylsulphonyl-D,L-aspartic acid,
108. N-Methyl-N-4-(1H-2-butyl-4-chloro-5-hydroxymethylimidazolylmethyl)phenylsulphonylglycine,
109. N-Methyl-N-4-(1H-2-butyl-4-chloro-5-hydroxymethylimidazolylmethyl)phenylsulphonyl-2,2-dimethylglycine,
110. N-Methyl-N-4-(1H-2-butyl-4-chloro-5-hydroxymethylimidazolylmethyl)phenylsulphonyl-1-aminocyclohexanecarboxylic acid,
111. N-Methyl-N-4-(1H-2-butyl-4-chloro-5-hydroxymethylimidazolylmethyl)phenylsulphonyl-D,L-alanine,
112. N-Ethyl-N-4-(1H-2-butyl-4-chloro-5-hydroxymethylimidazolylmethyl)phenylsulphonyl-D-phenylalanine, 113. N-Ethyl-N-4-(1H-2-butyl-4-chloro-5-hydroxymethylimidazolylmethyl)phenylsulphonyl-L-phenylalanine,
114. N-Methyl-N-4-(1H-2-butyl-4-chloro-5-hydroxymethylimidazolylmethyl)phenylsulphonyl-L-valine,
115. N-Methyl-N-4-(1H-2-butyl-4-chloro-5-hydroxymethylimidazolylmethyl)phenylsulphonyl-D-valine,
116. N-Methyl-N-4-(1H-2-butyl-4-chloro-5-hydroxymethylimidazolylmethyl)phenylsulphonyl-D,L-t-butylglycine,
117. N-Methyl-N-4-(1H-2-butyl-4-chloro-5-hydroxymethylimidazolylmethyl)phenylsulphonyl-L-leucine,
118. N-Methyl-N-4-(1H-2-butyl-4-chloro-5-hydroxymethylimidazolylmethyl)phenylsulphonyl-D-leucine,
119. N-n-Propyl-N-4-(1H-2-butyl-4-chloro-5-hydroxymethyl imidazolylmethyl)phenylsulphonyl-L-isoleucine,
120. N-n-Propyl-N-4-(1H-2-butyl-4-chloro-5-hydroxymethylimidazolylmethyl)phenylsulphonyl-D-isoleucine,
121. N-Methyl-N-4-(1H-2-butyl-4-chloro-5-hydroxymethylimidazolylmethyl)phenylsulphonyl-D,L-norleucine,
122. N-Methyl-N-4-(1H-2-butyl-4-chloro-5-hydroxymethylimidazolylmethyl)phenylsulphonyl-O-methyl-L-tyrosine,
123. N-Methyl-N-4-(1H-2-butyl-4-chloro-5-hydroxymethylimidazolylmethyl)phenylsulphonyl-O-methyl-D-tyrosine,
124. N-Methyl-N-4-(1H-2-butyl-4-chloro-5-hydroxymethylimidazolylmethyl)phenylsulphonyl-O-benzyl-D,L-serine,
125. N-Methyl-N-4-(1H-2-butyl-4-chloro-5-hydroxymethylimidazolylmethyl)phenylsulphonyl-D,L-methionine,
126. N-Methyl-N-4-(1H-2-butyl-4-chloro-5-hydroxymethylimidazolylmethyl)phenylsulphonyl-D,L-aspartic acid,
127. N-4-(1H-2-n-Propylpyrrolo[2,3-b]pyridinylmethyl)phenylsulphonylglycine,
128. N-4-(2H-3-n-Propylisoquinol-1-onylmethyl)phenylsulphonyl-2,2-dimethylglycine,
129. N-4-(3H-2-n-Butyl-5-methylthieno[2,3-d]pyrimidin-4-onylmethyl)phenylsulphonyl-1-aminocyclohexanecarboxylic acid,
130. N-4-(3H-2-n-Butyl-6-methyl-5-phenylimidazo[1,2-b]-1,2,4-triazolylmethyl)phenylsulphonyl-D,L-alanine,
131. N-4-(1H-4-Chloro-2,6-dimethylpyrrolo[3,2-c]pyridinylmethyl)phenylsulphonyl-L-phenylalanine,
132. N-4-(1H-4-Chloro-2,6-dimethylpyrrolo[3,2-c]pyridinylmethyl)phenylsulphonyl-D-phenylalanine,
133. N-4-(7H-8-n-Butyl-3,7-dihydro-1,3-dimethylpurine-2,6-dionylmethyl)phenylsulphonyl-L-phenylalanine,
134. N-4-(7H-8-n-Butyl-3,7-dihydro-1,3-dimethylpurine-2,6-dionylmethyl)phenylsulphonyl-D-phenylalanine,
135. N-4-(1H-3,5-Dibutyl-1,2,4-triazolylmethyl)phenylsulphonyl-L-valine,
136. N-4-(1H-3,5-Dibutyl-1,2,4-triazolylmethyl)phenylsulphonyl-D-valine,
137. N-4-(3H-2-n-Butyl-6-(1-hydroxy-1-methylethyl)quinazolin-4-onylmethyl)phenylsulphonyl-D,L-t-butylglycine,
138. N-4-(7H-2,4-Dimethyl-5,7-dihydropyrrolo[2,3-d]pyrimidin-6-onylmethyl)phenylsulphonyl-L-leucine,
139. N-4-(7H-2,4-Dimethyl-5,7-dihydropyrrolo[2,3-d]pyrimidin-6-onylmethyl)phenylsulphonyl-D-leucine,
140. N-4-(1H-2-n-Propyl-4-chloro-5-formylimidazolylmethyl)phenylsulphonyl-L-isoleucine,
141. N-4-(1H-2-n-Propyl-4-chloro-5-formylimidazolylmethyl)phenylsulphonyl-D-isoleucine,
142. N-Methyl-N-4-(3H-2-ethyl-5,7-dimethylimidazo[4,5-b]pyridinylmethyl)phenylsulphonylglycine,
143. N-Methyl-N-4-(3H-2-ethyl-5,7-dimethylimidazo[4,5-b]pyridinylmethyl)phenylsulphonyl-2,2-dimethylglycine,
144. N-Methyl-N-4-(3H-2-ethyl-5,7-dimethylimidazo[4,5-b]pyridinylmethyl)phenylsulphonyl-1-aminocyclohexanecarboxylic acid,
145. N-Methyl-N-4-(3H-2-ethyl-5,7-dimethylimidazo[4,5-b]pyridinylmethyl)phenylsulphonyl-D,L-alanine,
146. N-4-(3H-2-Ethyl-5,7-dimethylimidazo[4,5-b]pyridinylmethyl)phenylsulphonyl-D,L-alanine,
147. N-Methyl-N-4-(3H-2-ethyl-5,7-dimethylimidazo[4,5-b]pyridinylmethyl)phenylsulphonyl-D,L-alanine,
148. N-Methyl-N-4-(4H-3-ethylthio-1,2,4-benzothiadiazinedioxidemethyl)phenylsulphonyl-D-phenylalanine,
149. N-Methyl-N-4-(4H-3-ethylthio-1,2,4-benzothiadiazinedioxidemethyl)phenylsulphonyl-L-phenylalanine,
150. N-Methyl-N-4-(4H-3-n-butyl-5-(4-chlorobenzylthio)-1,2,4-triazolylmethyl)phenylsulphonyl-L-valine,
151. N-Methyl-N-4-(4H-3-n-butyl-5-(4-chlorobenzylthio)-1,2,4-triazolylmethyl)phenylsulphonyl-D-valine,
152. N-Methyl-N-4-(1H-2-n-butyl-4-chloro-1,6-dihydro-5-hydroxycarbonyl-6-methylpyrimidinylmethyl)phenylsulphonyl-D,L-t-butylglycine,
153. N-Methyl-N-4-(1H-2-n-butyl-4-trifluoromethyl-5-hydroxycarbonylimidazolylmethyl)phenylsulphonyl-D-leucine,
154. N-Methyl-N-4-(1H-2-n-butyl-4-trifluoromethyl-5-hydroxycarbonylimidazolylmethyl)phenylsulphonyl-L-leucine,
155. N-Methyl-N-4-(3H-2-ethylpyrimidin-4-onylmethyl)phenylsulphonyl-L-isoleucine,
156. N-Methyl-N-4-(3H-2-ethylpyrimidin-4-onylmethyl)phenylsulphonyl-D-isoleucine,
157. N-Methyl-N-4-(1H-2-n-propylpyrrolylmethyl)phenylsulphonyl-D,L-norleucine,
158. N-Methyl-N-4-(3H-2-n-butyl-6-methylpyrido[2,3-d]pyrimidin-4-onylmethyl)phenylsulphonyl-0-methyl-L-tyrosine,
159. N-Methyl-N-4-(3H-2-n-butyl-6-methylpyrido[2,3-d]pyrimidin-4-onylmethyl)phenylsulphonyl-0-methyl-D-tyrosine,
160. N-Methyl-N-4-(1H-3-n-butyl-1,4-dihydo-4-thioxoquinolinylmethyl)phenylsulphonyl-O-benzyl-D,L-serine,
161. N-Methyl-N-4-(1H-2-n-butyl-4-chloro-5-(3-methyl-1,2,4-oxadiazol-5-yl)imidazolylmethyl)-phenylsulphonyl-D,L-methionine,
162. N-Methyl-N-4-(1H-2-n-butyl-4-spirocyclopentane-2-imidazoline-5-onylmethyl)phenylsulphonyl-D,L-aspartic acid,
163. N-4-(1H-2-Butyl-4-chloro-5-hydroxymethylimidazolylmethyl)phenylsulphonyl-1-(1H-tetrazol-5-yl)methylamine,
164. N-Methyl-N-4-(1H-2-butyl-4-chloro-5-hydroxymethylimidazolylmethyl)phenylsulphonyl-1-methyl-1-(1H-tetrazol-5-yl)ethylamine,
165. N-Methyl-N-4-(1H-2-butyl-4-chloro-5-hydroxymethylimidazolylmethyl)phenylsulphonyl-1-(1H-tetrazol-5-yl)cyclohexylamine, 166. (S)-N-4-(1H-3,5-Dibutyl-1,2,4-triazolylmethyl) phenylsulphonyl-2-methyl-1-(1H-tetrazol-5-yl) propylamine,
167. (R)-N-4-(1H-3,5-Dibutyl-1,2,4-triazolylmethyl) phenylsulphonyl-2-methyl-1-(1H-tetrazol-5-yl) propylamine,
168. (S)-N-4-(1H-2-Butyl-4-chloro-5-formylimidazolylmethyl)phenylsulphonyl-2-methyl-1-(1H-tetrazol-5-yl)butylamine,
169. (R)-N-4-(1H-2-Butyl-4-chloro-5-formylimidazolylmethyl)phenylsulphonyl-2-methyl-1-(1H-tetrazol-5-yl)butylamine,
170. N-Methyl-N-4-(1H-2-n-butyl-4-chloro-1,6-dihydro-5-hydroxycarbonyl-6-methylpyrimidinylmethyl) phenylsulphonyl-2,2-dimethyl-1-(1H-tetrazol-5-yl) propylamine,
171. N-Methyl-N-4-(1H-2-butyl-4-chloro-5-hydroxymethylimidazolylmethyl)phenylsulphonyl-1-(1H-tetrazol-5-yl)ethylamine,
172. (S)-N-Ethyl-N-4-(1H-2-butyl-4-chloro-5-hydroxymethylimidazolylmethyl)phenylsulphonyl-1-phenyl-1-(1H-tetrazol-5-yl)methylamine,
173. (R)-N-Ethyl-N-4-(1H-2-butyl-4-chloro-5-hydroxymethylimidazolylmethyl)phenylsulphonyl-1-phenyl-1-(1H-tetrazol-5-yl)methylamine,
174. (S)-N-Methyl-N-4-(1H-2-butyl-4-chloro-5-hydroxymethylimidazolylmethyl)phenylsulphonyl-1-methyl-1-(1H-tetrazol-5-y l)ethylamine,
175. (R)-N-Methyl-N-4-(1H-2-butyl-4-chloro-5-hydroxymethylimidazolylmethyl)phenylsulphonyl-1-methyl-1-(1H-tetrazol-5-yl)ethylamine,
176. N-Methyl-N-4-(1H-2-butyl-4-chloro-5-hydroxymethylimidazolylmethyl)phenylsulphonyl-2,2-dimethyl-1-(1H-tetrazol-5-yl)-propylamine,
177. N-4-(1H-2-Butyl-4-chloro-5-hydroxymethylimidazolylmethyl) phenylsulphonylglycine 1H-tetrazol-5-ylamide,
178. N-4-(1H-2-Butyl-4-chloro-5-hydroxymethylimidazolylmethyl)phenylsulphonyl-2,2-dimethylglycine 1H-tetrazol-5-ylamide,
179. N-4-(1H-2-Butyl-4-chloro-5-hydroxymethylimidazolylmethyl)phenylsulphonyl-D,L-alanine 1H-tetrazol-5-ylamide,
180. N-4-(1H-2-Butyl-4-chloro-5-hydroxymethylimidazolylmethyl)phenylsulphonyl-D-phenylalanine 1H-tetrazol-5-ylamide,
181. N-4-(1H-2-Butyl-4-chloro-5-hydroxymethylimidazolylmethyl)phenylsulphonyl-L-phenylalanine 1H-tetrazol-5-ylamide,
182. N-4-(1H-2-Butyl-4-chloro-5-hydroxymethylimidazolylmethyl)phenylsulphonyl-L-valine trifluoromethylsulphonylamide,
183. N-4-(1H-2-Butyl-4-chloro-5-hydroxymethylimidazolylmethyl)phenylsulphonyl-D-valine trifluoromethylsulphonylamide,
184. N-4-(1H-2-Butyl-4-chloro-5-hydroxymethylimidazolylmethyl)phenylsulphonyl-D,L-t-butylglycine 1H-tetrazol-5-ylamide,
185. N-4-(1H-2-Butyl-4-chloro-5-hydroxymethylimidazolylmethyl)phenylsulphonyl-D-leucine methylsulphonylamide,
186. N-4-(1H-2-Butyl-4-chloro-5-hydroxymethylimidazolylmethyl)phenylsulphonyl-D-leucine methylsulphonylamide,
187. N-Methyl-N-4-(3H-2-ethyl-5,7-dimethylimidazo[4,5-b]pyridinylmethyl)phenylsulphonylglycine 1H-tetrazol-5-ylamide,
188. N-Methyl-N-4-(3H -2-ethyl-5,7-dimethylimidazo[4,5-b]pyridinylmethyl)phenylsulphonyl-2,2-dimethylglycine 1H-tetrazol-5-ylamide,
189. N-Methyl-N-4-(3H-2-ethyl-5,7-dimethylimidazo[4,5-b]pyridinylmethyl)phenylsulphonyl-D,L-alanine 1H-tetrazol-5-ylamide,
190. N-4-(3H-2-Ethyl-5,7-dimethylimidazo[4,5-b] pyridinylmethyl)phenylsulphonyl-D,L-alanine 1H-tetrazol-5-ylamide,
191. N-Methyl-N-4-(3H-2-ethyl-5,7-dimethylimidazo[4,5-b]pyridinylmethyl)phenylsulphonyl-D,L-alanine 1H-tetrazol-5-ylamide,
192. N-Methyl-N-4-(4H-3-ethylthio-1,2,4-benzothiadiazinedioxidemethyl)phenylsulphonyl-D-phenylalanine trifluoromethylsulphonylamide,
193. N-Methyl-N-4-(4H-3-ethylthio-1,2,4-benzothiadiazinedioxidemethyl)phenylsulphonyl-L-phenylalanine trifluoromethylsulphonylamide,
194. N-Methyl-N-4-(1H-2-butyl-4-chloro-5-hydroxymethylimidazolylmethyl) phenylsulphonylglycine 1H-tetrazol-5-ylamide,
195. N-Methyl-N-4-(1H-2-butyl-4-chloro-5-hydroxymethylimidazolylmethyl)phenylsulphonyl-2,2-dimethylglycine 1H-tetrazol-5-ylamide,
196. N-Methyl-N-4-(1H-2-butyl-4-chloro-5-hydroxymethylimidazolylmethyl)phenylsulphonyl-D,L-alanine 1H-tetrazol-5-ylamide,
197. N-Ethyl-N-4-(1H-2-butyl-4-chloro-5-hydroxymethylimidazolylmethyl)phenylsulphonyl-D-phenylalanine 1H-tetrazol-5-ylamide,
198. N-Ethyl-N-4-(1H-2-butyl-4-chloro-5-hydroxymethylimidazolylmethyl)phenylsulphonyl-L-phenylalanine 1H-tetrazol-5-ylamide,
199. N-Methyl-N-4-(1H-2-butyl-4-chloro-5-hydroxymethylimidazolylmethyl)phenylsulphonyl-L-valine trifluoromethylsulphonylamide,
200. N-Methyl-N-4-(1H-2-butyl-4-chloro-5-hydroxymethylimidazolylmethyl)phenylsulphonyl-D-valine trifluoromethylsulphonylamide,
201. N-Methyl-N-4-(1H-2-butyl-4-chloro-5-hydroxymethylimidazolylmethyl)phenylsulphonyl-D,L-t-butylglycine trifluoromethylsulphonylamide,
202. N-Methyl-N-4-(1H-2-butyl-4-chloro-5-hydroxymethylimidazolylmethyl)phenylsulphonyl-L-leucine 1H-tetrazol-5-ylamide,
203. N-Methyl-N-4-(1H-2-butyl-4-chloro-5-hydroxymethylimidazolylmethyl)phenylsulphonyl-D-leucine 1H-tetrazol-5-ylamide.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating a compound represented by general formula II

BH         II wherein B is as defined in general formula I, with a suitable base (e.g. sodium hydride, potassium hydride, sodium bis (trimethylsilyl)amide, potassium hydroxide or sodium methoxide), followed by a compound of general formula III

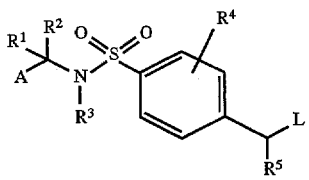

III wherein $R^1$, $R^2$, $R^3$, $R^4$, $R^5$ and A are as defined in general formula I, and L is a leaving group such as chloro, bromo, iodo, methanesulphonyloxy, p-toluenesulphonyloxy or trifluoromethanesulphonyloxy; or (b) optionally after step (a), converting, in one or a plurality of steps, a compound of general formula I into another compound of general formula I.

The reaction of step (a) can for preference be conducted in an aprotic solvent (e.g. tetrahydrofuran, N,N-dimethylformamide or acetonitrile) to yield compounds of general formula I. In the case where an unsymmetrically substituted derivative B is used the reaction can yield an isomeric mixture, which is separated by chromatography to yield compounds of general formula I.

By means of step (b), compounds of general formula I wherein A is a $-CO_2R^6$ group can be convened to compounds of general formula I in which A is a $-CO_2H$ group by acid or base catalysed hydrolysis in a protic solvent. Suitable acids for use in the hydrolysis include sulphuric and hydrochloric acids, whilst base hydrolysis can be catalysed with sodium or potassium hydroxide.

If A represents a $-CO_2R^6$ group in which $R^6$ is a benzyl group, the conversion of A from an ester to an acid can also be effected by hydrogenation in a suitable solvent, for example, a lower alcohol such as ethanol using a noble metal catalyst such as palladium or platinum.

Also by means of step (b), compounds of general formula I in which A is a $-CO_2R^6$ group can be convened to compounds of general formula I in which A represents a $-CH_2OH$ group by reduction using any suitable method although lithium aluminium hydride or diisobutyl aluminium hydride in an aprotic solvent such as diethyl ether or toluene have proved to be particularly appropriate reducing agents.

Also by means of step (b), compounds of general formula I wherein A is a $-C(=O)NHY$ or $-C(=O)NR^9R^{10}$ group wherein Y, $R^9$ and $R^{10}$ are as defined for general formula I, may be prepared by treatment of a compound of general formula I wherein A is $-CO_2R^6$ wherein $R^6$ is hydrogen by treatment with an amine of general formula $H_2NY$ or $HNR^9R^{10}$ in the presence of a coupling reagent (e.g. 1,3-dicyclohexylcarbodiimide).

Also by means of step (b), compounds of general formula I wherein A is a $-C(=O)NHSO_2R^6$ wherein $R^6$ is as defined for general formula I, may be prepared by activation of a compound of general I wherein A is $-CO_2R^6$ wherein $R^6$ is hydrogen by conversion to the acid chloride or acyl imidazole followed by treatment with an alkali metal salt of a sulphonamide of general formula $H_2NSO_2R^6$.

Also by means of step (b), compounds of general formula I wherein A is a group Y wherein Y is a tetrazol-5-yl group may be prepared by the treatment of a compound of general I wherein A is $-C(=O)NR^9R^{10}$ group wherein $R^9$ is hydrogen and $R^{10}$ is $-CH_2CH_2CN$ with triphenylphosphine, diethyl azodicarboxylate and azidotrimethylsilane according to the procedure described by V. Duncia, M. E. Pierce and J. B. Santella III, *J. Org. Chem.*, 1991, 56, 2395-2400.

Derivatives of general formula II are generally available or may be prepared by a number of methods known to those skilled in the art.

Compounds of general formula III may be prepared by treatment of an amine of general formula IV

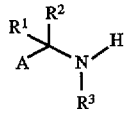

IV wherein $R^1$, $R^2$, $R^3$ and A are as defined in general formula I, with a sulphonyl halide of general formula V

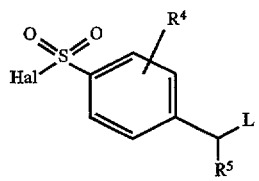

V wherein $R^4$ and $R^5$ are as defined in general formula I, L is a leaving group such as chloro, bromo, iodo, methanesulphonyloxy, p-toluenesulphonyloxy or trifluoromethanesulphonyloxy and Hal is a halide (e.g. fluoro, chloro or bromo), in the presence of a suitable base (e.g. triethylamine). Amines of general formula IV and sulphonyl halides of general formula V are known in the art or may be prepared by methods known in the art.

The appropriate solvents employed in the above reactions are solvents wherein the reactants are soluble but do not react with the reactants. The preferred solvents vary from reaction to reaction and are readily ascertained by one of ordinary skill in the art.

Compounds of general formula III are valuable intermediates in the preparation of compounds of general formula I, as are other novel compounds specifically or generically disclosed herein. Therefore, according to a third aspect of the invention, there is provided a compound of general formula III.

Compounds of general formula I are potentially useful both as PAF antagonists and as antagonists of angiotensin II.

This invention also relates to methods of treatment for patients (or animals including mammalian animals raised in the dairy, meat, or fur trades, or as pets) suffering from disorders or diseases which can be attributed to PAF or to angiotensin II as previously described. More specifically, the invention relates to a method of treatment involving the administration of PAF antagonists of general formula I as the active ingredient and also to a method of treatment involving the administration of angiotensin II antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a fourth aspect of the invention there is provided a compound of general formula I for use in human or veterinary medicine particularly in the management of diseases mediated by PAF or by angiotensin II. When used as PAF antagonists, the compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions. When used as angiotensin II antagonists, the compounds of general formula I can be used in the treatment of conditions such as hypertension, congestive heart failure, glaucoma and intraocular hypertension, cognitive dysfunction and psoriasis although they also have potential in the treatment of other conditions.

According to a fifth aspect of the invention there is provided the use of a compound of general formula I in the preparation of an agent for the treatment or prophylaxis of PAF-mediated diseases, and/or the treatment of inflammatory disorders such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

According to a further aspect of the invention, there is provided the use of a compound of general formula I in the preparation of an agent for the treatment or prophylaxis of diseases and conditions mediated by angiotensin II. This includes the preparation of an agent for the treatment of the conditions mentioned above, particularly elevated blood pressure.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to yet another aspect of the invention there is provided a pharmaceutical or veterinary formulation comprising a compound of general formula I and a pharmaceutically and/or veterinarily acceptable carder. One or more compounds of general formula I may be present in association with one or more non-toxic pharmaceutically and/or veterinarily acceptable carders and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug, depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacologically active ingredient, in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid nonionic or anionic surfactants and/or diluents. Pharmaceutical compositions in which the pharmacologically active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carder material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF and to angiotensin II. Compounds of general formula I inhibit PAF-induced and angiotensin H induced functions in both the cellular and tissue levels by changing the PAF binding to its specific receptor site and the binding of angiotensin II to its specific receptor. The ability of compounds of general formula I to inhibit the binding of PAF to its specific receptor binding site on human platelet plasma membranes was measured according to Example 204. The angiotensin II antagonist activity of compounds of general formula I is demonstrated in vitro by their ability to inhibit the contraction of rabbit aorta rings caused by angiotensin II was measured according to Example 205. The attached drawing FIG. 1, shows inhibition of angiotensin II induced contraction of rabbit aorta rings.

The following examples illustrate the invention, but are not intended to limit the scope in any way.

The following abbreviations have been used in the Examples:

DCM-Dichloromethane
DIPE-Diisopropylether
DMF-N,N-Dimethylformamide
NBS-N-Bromosuccinimide
TDA-1-Tris(2-(2-methoxyethoxy)ethyl)amine
THF-Tetrahydrofuran Unless otherwise stated $^1$H NMR and $^{13}$C NMR spectra were recorded on a Bruker AC-250 spectrometer at 250 MHz and 62.9 MHz respectively using CDCl$_3$ as a solvent and internal reference and are reported as delta ppm from TMS.

EXAMPLE 1

N-4-(1H-2-Phenylimidazolylmethyl)phenylsulphonyl-L-leucine ethyl ester

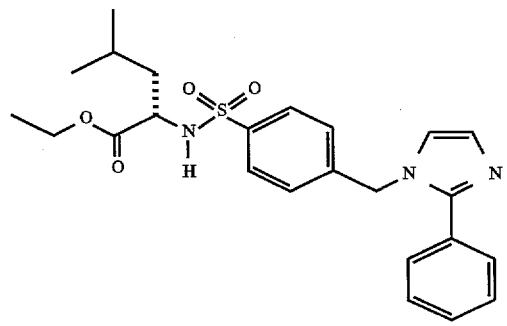

(a) 4-Bromomethylphenylsulphonylchloride

To a solution of p-toluenesulphonyl chloride (50 g, 0.26 mol) in benzene (150 ml) and NBS (46.7 g, 0.26 mol) heated at reflux was added 2,2'-azobis(2-methylpropionitrile) (100 mg). The mixture was heated at reflux for 12 h and allowed to cool to room temperature. The white precipitate of succinimide that formed was separated and discarded. The filtrate was taken up in DCM (200 ml) and washed with

23 water (3×100 ml) followed by brine (100 ml) and dried over anhydrous sodium sulphate. Filtration, concentration and subsequent crystallisation (from DIPE) gave in two crops 4-bromomethylphenylsulphonylchloride (46.3 g, 66%) as a white crystalline solid.

m.p. 75°–76° C.

delta$_H$ 8.02 (2H, d, J 8.5 Hz), 7.64 (2H, d, J 8.5 Hz), 4.52 (2H, s).

(b) N-4-Bromomethylphenylsulphonyl-L-leucine ethyl ester

L-leucine ethyl ester hydrochloride (75.0 g, 0.403 mol) was suspended in THF (300 ml) at 0° C., and triethylamine (67 ml, 0.484 mol) added slowly. After stirring for 15 mins a solution of 4-bromomethylsulphonyl chloride (108.4 g, 0.403 mol) in THF (100 ml) was added via cannula. The reaction mixture was allowed to stir overnight at ambient temperature. The solvent was removed under low pressure and the organics were extracted into ethyl acetate (200 ml) and washed with water (100 ml) and brine (100 ml). The organic portion was dried over anhydrous magnesium sulphate, filtered and the solvent evaporated under low pressure. The product was recrystallised from DIPE (500 ml) to give N-4-bromomethylphenylsulphonyl-L-leucine ethyl ester (134g, 85%) as a white crystalline solid.

delta$_H$ 7.84 (2H, d, J 8.3 Hz), 7.52 (2H, d, J 8.3 Hz), 5.06 (1H, d, J 10.1 Hz), 4.61 (2H, s), 3.97–3.82 (3H, m), 1.85–1.79 (1H, m), 1.49 (2H, t, J 7.1 Hz), 1.08 (3H, t, J 7.1 Hz), 0.92 (3H, d, J 6.7 Hz), 0.91 (3H, d, J 6.5 Hz).

(c) N-4-(1H-2-Phenylimidazolylmethyl)phenylsulphonyl-L-leucine ethyl ester

Sodium hydride (60% dispersion in oil: 197 mg, 4.92 mmol) was added to a stirred solution of 2-phenylimidazole (710 mg, 4.92 mmol) in dry THF (60 ml) under argon at room temperature. After 2 h a solution of N-4-bromomethylphenylsulphonyl-L-leucine ethyl ester (2.0 g, 4.92 mmol) in dry THF (60 ml) was added. The mixture was stirred for 8 h and saturated ammonium chloride (200 ml) was added and the product extracted with ethyl acetate (3×150 ml). The combined organic layers were washed with water (2×100 ml), dried over anhydrous sodium sulphate, filtered and the solvent removed. Chromatography (silica: 5% methanol in DCM) gave N-4-(1H-2-phenylimidazolylmethyl)phenylsulphonyl-L-leucine ethyl ester (1.0 g, 45%) as a white foam.

Analysis calculated for $C_{24}H_{29}N_3O_4S.0.5H_2O$ Requires C 62.05 H 6.51 N 9.04 Found C 62.06 H 6.30 N 9.18 i.r. (CDCl$_3$) 1730, 1340, 1155 cm$^{-1}$ delta$_H$ 7.76 (2H, d, J 8.3 Hz), 7.50–7.42 (2H, m), 7.40–7.32 (3H, m), 7.19 (1H, d, J 1.3 Hz), 7.12 (2H, d, J 8.3 Hz), 6.93 (1H, d, J 1.0 Hz), 5.90 (1H, d, J 9.9 Hz), 5.26 (2H, s), 3.95–3.72 (3H, m), 1.80–1.62 (1H, m), 1.50–1.38 (2H, m), 1.03 (3H, t, J 7.2 Hz), 0.84 (3H, d, J 5.2 Hz), 0.81 (3H, d, J 5.0 Hz).

24

EXAMPLE 2

N-Methyl-N-4-(1H-2-nitroimidazolylmethyl)phenylsulphonyl-L-leucine ethyl ester

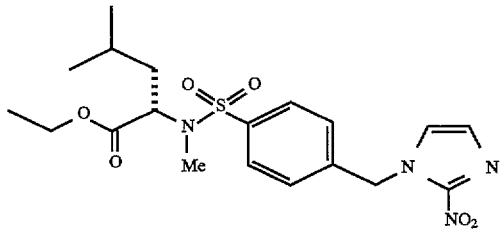

(a) N-Methyl-N-4-bromomethylphenylsulphonyl-L-leucine ethyl ester

N-4-Bromomethylphenylsulphonyl-L-leucine ethyl ester (2.0 g, 5.1 mmol) was dissolved in dry THF (30 ml) under argon and cooled to 0° C. Sodium hydride (60% dispersion in oil: 200 mg, 5.1 mmol) was added followed by methyl iodide (0.64 ml, 10.2 mmol) after a period of 5 mins. The reaction mixture was allowed to warm to room temperature and was stirred overnight. The reaction mixture was quenched with saturated aqueous ammonium chloride (30 ml) and extracted with ethyl acetate (2×50 ml). The combined organic extracts were washed with brine (50 ml), dried over anhydrous sodium sulphate, filtered and evaporated to give N-methyl-N-4-bromomethylphenylsulphonyl-L-leucine ethyl ester as an orange oil which was used directly in the next step without further purification.

delta$_H$ 7.81 (2H, d, J 8.5 Hz), 7.52 (2H, d, J 8.5 Hz), 4.66 (1H, dd, J 9.3, 7.4 Hz), 4.62 (2H, s), 3.99–3.79 (2H, m), 2.87 (3H, s), 1.74–1.58 (3H, m), 1.07 (3H, t, J 7.3 Hz), 0.99 (3H, d, J 5.2 Hz), 0.97 (3H, d, H, J 6.0 Hz).

(b) N-Methyl-N-4-(1H-2-nitroimidazolylmethyl)phenylsulphonyl-L-leucine ethyl ester A solution of 1M sodium bis(trimethylsilyl)amide (4.42 ml, 4.42 mmol) was added to a stirred solution of 2-nitroimidazole (500 mg, 4.42 mmol) in a mixture of dry THF (50 ml) and dry DMF (5 ml) at room temperature under argon. After 15 min a solution of N-methyl-N-4-bromomethylphenylsulphonyl-L-leucine ethyl ester (1.80 g, 4.42 mmol) in dry THF (10 ml) was added and the reaction mixture was stirred at room temperature overnight. The solvent was removed under reduced pressure and the residue was extracted into ethyl acetate and washed with aqueous ammonium chloride, brine, dried over anhydrous sodium sulphate, filtered and evaporated. Chromatography (silica: 2% methanol in DCM) gave N-methyl-N-4-(1H-2-nitroimidazolylmethyl)phenylsulphonyl-L-leucine ethyl ester (0.39 g, 73%) as a pale yellow oil.

i.r. (CDCl$_3$) 2960, 1730, 1540, 1480, 1335, 1155 cm–1 delta$_H$ 7.57 (2H, d, J 8.4 Hz), 7.23 (1H, d, J 0.7 Hz), 7.15 (2H, d, J 8.3 Hz), 7.03 (1H, d, J 0.8 Hz), 5.56 (2H, s), 4.44 (1H, t, J 6.7 Hz), 3.66 (2H, m), 2.68 (3H, s), 1.45 (3H, m), 0.97–0.78 (9H, m);

delta$_C$ 169.20, 143.03, 138.17, 137.61, 129.92, 127.76, 127.16, 126.38, 126.09, 125.50, 59.48, 55.78, 51.09, 36.50, 28.39, 22.85, 21.48, 19.57, 12.34.

EXAMPLE 3

N-4-(1H-4,5-Diphenylimidazolylmethyl) phenylsulphonyl-L-leucinyl ethyl ether

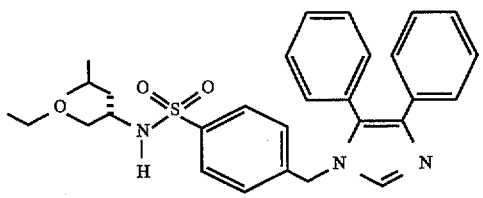

(a) L-Leucinyl ethyl ester

Sodium hydride (60% dispersion in oil: 4.5 g, 0.11 mol) was added to a stirred solution of L-leucinol (12.8 ml, 0.10 mol) in a mixture of dry acetonitrile (24 ml) and dry THF (200 ml) at room temperature under argon. The mixture was heated at reflux for 2 h, cooled to 55° C. and ethyl iodide (8.2 ml, 0.10 mol) added carefully. The reaction mixture was heated at reflux overnight and allowed to cool to room temperature. Ice cold brine (100 ml) was added carefully and the mixture extracted with ethyl acetate (3×100 ml). The combined organic extracts were dried over anhydrous sodium sulphate, filtered and evaporated. The residue was distilled under reduced pressure to give L-leucinyl ethyl ether (4.5 g, 30%) as a colourless oil which was used directly in the next step.

delta$_H$ 3.49–3.14 (4H, m), 3.08–2.81 (2H, m), 1.73–1.50 (1H, m), 1.16–0.91 (6H, m), 0.84 (3H, d, J 6.9 Hz), 0.81 (3H, d, J 6.7 Hz).

(b) N-4-Bromomethylphenylsulphonyl-L-leucinyl ethyl ether

N-4-Bromomethylphenylsulphonyl-L-leucinyl ethyl ether was prepared by the procedure described in Example 1 Step (b) employing L-leucinyl ethyl ether in lieu of L-leucine ethyl ester hydrochloride.

White crystalline solid (68% yield): m.p. 70° C.

i.r. (CDCl$_3$) 3380, 2960, 2870, 1410, 1365, 1155, 1115 cm$^{-1}$ delta$_H$ 7.85 (2H, d, J 8.4 Hz), 7.49 (2H, d, J 8.3 Hz), 5.02 (1H, d, J 8.4 Hz), 4.48 (2H, s), 3.47–3.20 (5H, m), 1.56 (1H, m), 1.45–1.20 (2H, m), 1.04 (3H, t, J 7.0 Hz), 0.82 (3H, d, J 6.6 Hz), 0.74 (3H, d, J 6.5 Hz).

(c) N-4-(1H-4,5-Diphenylimidazolylmethyl) phenylsulphonyl-L-leucinyl ethyl ether N-4-(1H-4,5-Diphenylimidazolylmethyl) phenylsulphonyl-L-leucinyl ethyl ether was prepared by the procedure of Example 1 Step (c) employing 4,5-diphenylimidazole in lieu of 2-phenylimidazole and N-4-bromomethylphenylsulphonyl-L-leucinyl ethyl ether in lieu of N-4-bromomethylphenylsulphonyl-L-leucine ethyl ester.

Colourless oil (5% yield for last step after chromatography (silica: 3% methanol in DCM)):

i.r. (CDCl$_3$) 2210, 1605, 1410, 1335, 1120 cm$^{-1}$ delta$_H$ 7.78 (2H, d, J 8.4 Hz), 7.54–7.29 (6H, m), 7.16–7.10 (5H, m), 7.04 (2H, d, J 8.3 Hz), 5.16 (1H, d, J 8.4 Hz), 5.05 (2H, s), 3.48–3.10 (5H, m), 1.54–1.20 (3H, m), 1.05 (3H, t, J 7.0 Hz), 0.82 (3H, d, J 6.5 Hz), 0.75 (3H, d, J 6.5 Hz);

delta$_C$ 141.23, 141.08, 137.04, 134.07, 130.72, 130.02, 129.00, 128.90, 128.56, 128.12, 127.89, 127.46, 127.08, 126.50, 71.81, 66.51, 51.95, 48.09, 41.63, 24.28, 22.75, 21.91, 14.86.

EXAMPLE 4

N-4-(1H-2-Butyl-4-chloro-5-hydroxymethylimidazolylmethyl)phenylsulphonyl-L-leucine ethyl ester

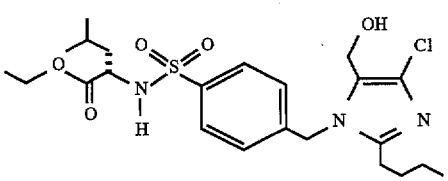

N-4-(1H-2-Butyl-4-chloro-5-hydroxymethylimidazolylmethyl)phenylsulphonyl-L-leucine ethyl ester was prepared by the procedure of Example 2 Step (b) employing 2-butyl-4-chloro-5-hydroxymethylimidazole in lieu of 2-nitroimidazole and N-4-bromomethylphenylsulphonyl-L-leucine ethyl ester in lieu of N-methyl-N-4-bromomethylphenylsulphonyl-L-leucine ethyl ester. 2-Butyl-4-chloro-5-hydroxymethylimidazole was prepared by the procedure described in U.S. Pat. No. 4,355,040.

Colourless oil (30% yield for last step after chromatography (silica: 5% methanol in DCM)):

i.r. (CDCl$_3$) 1730, 1340, 1150 cm$^{-1}$ delta$_H$ 7.80 (2H, d, J 8.3 Hz), 7.11 (2H, d, J 8.3 Hz), 5.41 (1H, d, J 10.0 Hz), 5.14 (2H, s), 4.58 (2H, s), 3.98–3.78 (3H, m), 2.56 (2H, dd, J 8.2, 7.4 Hz), 1.83–1.52 (3H, m), 1.47 (2H, m), 1.40–1.25 (2H, m), 1.07 (3H, t, J 7.2 Hz), 0.91–0.80 (9H, m);

delta$_C$ 172.09, 148.09, 140.66, 139.69, 135.41, 127.96, 126.49, 113.99, 61.45, 55.96, 54.39, 46.41, 42.22, 29.63, 27.30, 24.25, 22.65, 22.29, 21.31, 13.89.

EXAMPLES 5–22

The compounds of Examples 5–22 may be prepared by the procedures of Example 1 Step (b) and Example 4 employing the appropriate amino acid derivative as starting material in lieu of L-leucine ethyl ester hydrochloride.

5. N-4-(1H-2-Butyl-4-chloro-5-hydroxymethylimidazolylmethyl) phenylsulphonylglycine methyl ester
6. N-4-(1H-2-Butyl-4-chloro-5-hydroxymethylimidazolylmethyl)phenylsulphonyl-2,2-dimethylglycine methyl ester
7. N-4-(1H-2-Butyl-4-chloro-5-hydroxymethylimidazolylmethyl)phenylsulphonyl-1-methoxycarbonylcyclohexylamine
8. N-4-(1H-2-Butyl-4-chloro-5-hydroxymethylimidazolylmethyl)phenylsulphonyl-D,L-alanine methyl ester
9. N-4-(1H-2-Butyl-4-chloro-5-hydroxymethylimidazolylmethyl)phenylsulphonyl-D-phenylalanine methyl ester
10. N-4-(1H-2-Butyl-4-chloro-5-hydroxymethylimidazolylmethyl)phenylsulphonyl-L-phenylalanine methyl ester
11. N-4-(1H-2-Butyl-4-chloro-5-hydroxymethylimidazolylmethyl)phenylsulphonyl-L-valine methyl ester
12. N-4-(1H-2-Butyl-4-chloro-5-hydroxymethylimidazolylmethyl)phenylsulphonyl-D-valine methyl ester
13. N-4-(1H-2-Butyl-4-chloro-5-hydroxymethylimidazolylmethyl)phenylsulphonyl-D,L-t-butylglycine methyl ester 14. N-4-(1H-2-Butyl-4-chloro-5-hydroxymethylimidazolylmethyl)phenylsulphonyl-D-leucine ethyl ester
15. N-4-(1H-2-Butyl-4-chloro-5-hydroxymethylimidazolylmethyl)phenylsulphonyl-L-isoleucine ethyl ester
16. N-4-(1H-2-Butyl-4-chloro-5-hydroxymethylimidazolylmethyl)phenylsulphonyl-D-isoleucine ethyl ester
17. N-4-(1H-2-Butyl-4-chloro-5-hydroxymethylimidazolylmethyl)phenylsulphonyl-D,L-norleucine ethyl ester
18. N-4-(1H-2-Butyl-4-chloro-5-hydroxymethylimidazolylmethyl)phenylsulphonyl-O-methyl-L-tyrosine methyl ester
19. N-4-(1H-2-Butyl-4-chloro-5-hydroxymethylimidazolylmethyl)phenylsulphonyl-O-methyl-D-tyrosine methyl ester
20. N-4-(1H-2-Butyl-4-chloro-5-hydroxymethylimidazolylmethyl)phenylsulphonyl-O-benzyl-D,L-serine methyl ester
21. N-4-(1H-2-Butyl-4-chloro-5-hydroxymethylimidazolylmethyl)phenylsulphonyl-D,L-methionine methyl ester
22. N-4-(1H-2-Butyl-4-chloro-5-hydroxymethylimidazolylmethyl)phenylsulphonyl-D,L-aspartic acid diethyl ester

EXAMPLE 23

N-Methyl-N-4-(1H-2-butyl-4-chloro-5-hydroxymethylimidazolylmethyl)phenylsulphonyl-L-leucine ethyl ester

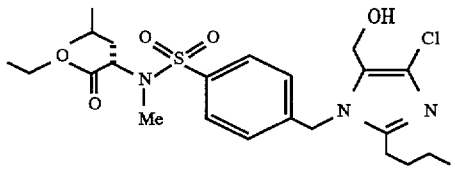

2-Butyl-4-chloro-5-hydroxymethylimidazole (1.50 g, 8 mmol) was dissolved in dry methanol (20 ml) under argon and sodium wire (184 mg, 8 mmol) was added. The reaction mixture was stirred at room temperature for 0.5 h and the solvent removed under reduced pressure. The residue was dissolved in dry DMF (40 ml) under argon and a solution of N-methyl-N-4-bromomethylphenylsulphonyl-L-leucine ethyl ester (3.25 g, 8 mmol) in DMF (5 ml) was added. The mixture was stirred overnight at 50° C. and evaporated to dryness and the residue partitioned between ethyl acetate and aqueous ammonium chloride. The organic extracts were washed with brine, dried over anhydrous sodium sulphate, filtered and evaporated. Column chromatography (silica: 3% methanol in DCM) gave N-methyl-N-4-(1H-2-butyl-4-chloro-5-hydroxymethylimidazolylmethyl) phenylsulphonyl-L-leucine ethyl ester (670 mg, 35%) as an off-white foam.

Analysis calculated for $C_{24}H_{36}ClN_3O_5S$ Requires C 56.07 H 7.06 N 8.17 Found C 55.86 H 7.05 N 8.19 i.r. (CDCl$_3$) 3600, 2960, 2220, 1735, 1340, 1255, 1150 cm$^{-1}$ delta$_H$ 7.70 (2H, d, J 8.3 Hz), 7.09 (2H, d, J 8.3 Hz), 5.27 (2H, s), 4.60 (1H, t, J 8.0 Hz), 4.40 (2H, br s), 3.94 (1H, br s), 3.86 (2H, q, J 7.1 Hz), 2.79 (3H, s), 2.46 (2H, dd, J 7.4, 7.4 Hz), 1.63–1.51 (5H, m), 1.34–1.22 (2H, m), 1.06 (3H, t, J 7.1 Hz), 0.93 (3H, d, J 6.0 Hz), 0.91 (3H, d, J 6.0 Hz), 0.82 (3H, t, J 7.3 Hz).

EXAMPLE 24

N-Methyl-N-4-(1H-2-butyl-4-chloro-5-hydroxymethylimidazolylmethyl)phenylsulphonyl-L-leucine n-propyl ester

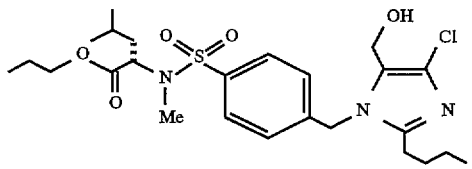

N-Methyl-N-4-(1H-2-butyl-4-chloro-5-hydroxymethylimidazolylmethyl)phenylsulphonyl-L-leucine n-propyl ester was prepared by the procedure of Example 23 employing N-methyl-N-4-bromomethylphenylsulphonyl-L-leucine n-propyl ester in lieu of N-methyl-N-4-bromomethylphenylsulphonyl-L-leucine ethyl ester. N-Methyl-N-4-bromomethylphenylsulphonyl-L-leucine n-propyl ester was prepared by the procedue of Example 1 Step (b) and Example 2 Step (a) employing L-leucine n-propyl ester hyrochloride as starting material.

Pale yellow solid (35% yield after chromatography (silica: 0–5% methanol in chloroform)): m.p. 36°–43° C Analysis calculated for $C_{25}H_{38}N_3ClO_5S$ Requires C 56.86 H 7.25 N 7.96 Found C 56.53 H 7.01 N 8.14 i.r. (nujol) 3540, 3200, 1730, 1600, 1545, 1250, 1146, 720 cm$^{-1}$ delta$_H$ 7.78 (2H, d, J 8.5 Hz), 7.12 (2H, d, J 8.5 Hz), 5.28 (2H, s), 4.68 (1H, t, J 7.8 Hz), 4.48 (2H, s), 3.87 (2H, dt, J 3.6, 2.2 Hz), 2.84 (3H, s), 2.56 (2H, t, J 7.5 Hz), 1.60–1.20 (9H, m), 1.10–0.85 (12H, m).

EXAMPLES 25–42

The compounds of Examples 25–42 may be prepared by the procedure of Example 24 employing the appropiate amino acid derivative in lieu of L-leucine n-propyl ester hyrochloride as starting material.

25. N-Methyl-N-4-(1H-2-butyl-4-chloro-5-hydroxymethylimidazolylmethyl) phenylsulphonylglycine methyl ester
26. N-Methyl-N-4-(1H-2-butyl-4-chloro-5-hydroxymethylimidazolylmethyl)phenylsulphonyl-2,2-dimethylglycine methyl ester
27. N-Methyl-N-4-(1H-2-butyl-4-chloro-5-hydroxymethylimidazolylmethyl)phenylsulphonyl-1-methoxycarbonylcyclohexylamine
28. N-Methyl-N-4-(1H-2-butyl-4-chloro-5-hydroxymethylimidazolylmethyl)phenylsulphonyl-D,L-alanine methyl ester
29. N-Ethyl-N-4-(1H-2-butyl-4-chloro-5-hydroxymethylimidazolylmethyl)phenylsulphonyl-D-phenylalanine methyl ester
30. N-Ethyl-N-4-(1H-2-butyl-4-chloro-5-hydroxymethylimidazolylmethyl)phenylsulphonyl-L-phenylalanine methyl ester
31. N-Methyl-N-4-(1H-2-butyl-4-chloro-5-hydroxymethylimidazolylmethyl)phenylsulphonyl-L-valine methyl ester
32. N-Methyl-N-4-(1H-2-butyl-4-chloro-5-hydroxymethylimidazolylmethyl)phenylsulphonyl-D-valine methyl ester
33. N-Methyl-N-4-(1H-2-butyl-4-chloro-5-hydroxymethylimidazolylmethyl)phenylsulphonyl-D,L-t-butylglycine methyl ester 34. N-Methyl-N-4-(1H-2-butyl-4-chloro-5-hydroxymethylimidazolylmethyl)phenylsulphonyl-D-leucine ethyl ester 35. N-n-Propyl-N-4-(1H-2-butyl-4-chloro-5-hydroxymethylimidazolylmethyl)phenylsulphonyl-L-isoleucine ethyl ester 36. N-n-Propyl-N-4-(1H-2-butyl-4-chloro-5-hydroxymethylimidazolylmethyl)phenylsulphonyl-D-isoleucine ethyl ester 37. N-Methyl-N-4-(1H-2-butyl-4-chloro-5-hydroxymethylimidazolylmethyl)phenylsulphonyl-D,L-norleucine ethyl ester 38. N-Methyl-N-4-(1H-2-butyl-4-chloro-5-hydroxymethylimidazolylmethyl)phenylsulphonyl-O-methyl-L-tyrosine methyl ester 39. N-Methyl-N-4-(1H-2-butyl-4-chloro-5-hydroxymethylimidazolylmethyl)phenylsulphonyl-O-methyl-D-tyrosine methyl ester 40. N-Methyl-N-4-(1H-2-butyl-4-chloro-5-hydroxymethylimidazolylmethyl)phenylsulphonyl-O-benzyl-D,L-serine methyl ester 41. N-Methyl-N-4-(1H-2-butyl-4-chloro-5-hydroxymethylimidazolylmethyl)phenylsulphonyl-D,L-methionine methyl ester 42. N-Methyl-N-4-(1H-2-butyl-4-chloro-5-hydroxymethylimidazolylmethyl)phenylsulphonyl-D,L-aspartic acid diethyl ester EXAMPLES 43 and 44

The compounds of Examples 43 and 44 were prepared from N-methyl-N-4-bromomethylphenylsulphonyl-L-leucine ethyl ester by the procedure of Example 23 employing the appropriate imidazole derivative in lieu of 2-butyl-4-chloro-5-hydroxymethylimidazole and methanol as a co-solvent to achieve transesterification.

43. N-Methyl-N-4-(1H-2-ethylimidazolylmethyl) phenylsulphonyl-L-leucine methyl ester

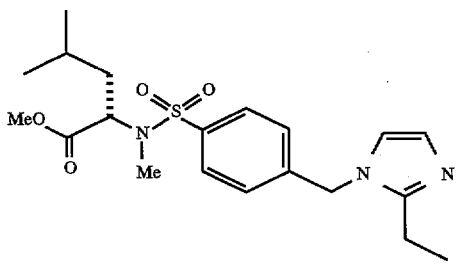

Colourless oil (91% yield after chromatography (2–5% methanol in DCM)):

i.r. (CDCl$_3$) 2960, 2200, 1740, 1340, 1150 cm$^{-1}$ delta$_H$ 7.74 (2H, d, J 8.5 Hz), 7.13 (2H, d, J 8.6 Hz), 7.01 (1H, d, J 1.2 Hz), 6.83 (1H, d, J 1.4 Hz), 5.13 (2H, s), 4.68–4.61 (1H, m), 3.43 (3H, s), 2.82 (3H, s), 2.59 (2H, q, J 7.5 Hz), 1.65–1.55 (3H, m), 1.27 (3H, t, J 7.5 Hz), 0.94 (3H, d, 6.0 Hz), 0.93 (3H, d, J 6.1 Hz);

delta$_C$ 171.29, 149.43, 141.38, 138.63, 127.90, 127.66, 126.72, 119.69, 56.96, 51.64, 48.70, 37.99, 29.72, 24.31, 22.94, 21.01, 20.02, 11.83.

44. N-Methyl-N-4-(1H-2-n-propylimidazolylmethyl) phenylsulphonyl-L-leucine methyl ester

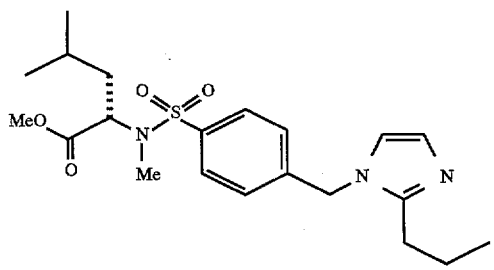

Colourless oil (51% yield after chromatography (2–4% methanol in DCM)):

Analysis calculated for C$_{21}$H$_{31}$N$_3$O$_4$S Requires C 59.83 H 7.41 N 9.97 Found C 60.04 H 7.44 N 9.95 i.r. (CDCl$_3$) 2960, 2200, 1740, 1600, 1410, 1345 cm$^{-1}$ delta$_H$ 7.64 (2H, d, J 8.2 Hz), 7.06 (2H, d, J 8.1 Hz), 6.90 (1H, s), 6.75 (1H, s), 5.07 (2H, s), 4.59–4.53 (1H, m), 3.34 (3H, s), 2.73 (3H, s), 2.46 (2H, t, J 7.6 Hz), 1.63 (2H, q, J 7.5 Hz), 1.55–1.50 (3H, m), 0.87–0.81 (9H, m).

EXAMPLE 45

(A) N-4-(3H-Imidazo[4,5-b]pyridylmethyl) phenylsulphonyl-L-leucinyl ethyl ether and (B) N-4-(1H-imidazo[4,5-b]pyridylmethyl)phenylsulphonyl-L-leucinyl ethyl ether

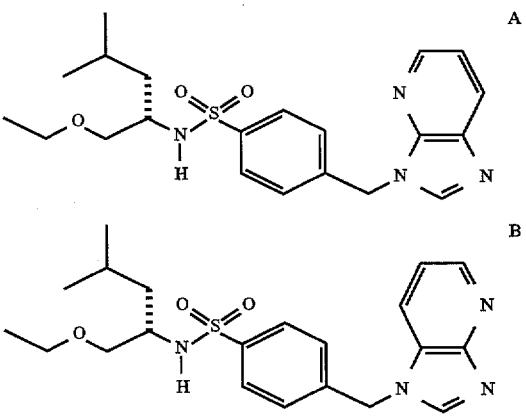

(A) N-4-(3H-Imidazo[4,5-b]pyridylmethyl) phenylsulphonyl-L-leucinyl ethyl ether and (B) N-4-(1H-imidazo[4,5-b]pyridylmethyl)phenylsulphonyl-L-leucinyl ethyl ether were prepared by the procedure of Example 1 Step (c) employing imidazo[4,5-b]pyridine in lieu of 2-phenylimidazole and N-4-bromomethylphenylsulphonyl-L-leucinyl ethyl ether in lieu of N-4-bromomethylphenylsulphonyl-L-leucine ethyl ester. The two regioisomers were separated by chromatography (silica: 5% methanol in DCM) eluting in the order:

Regioisomer (A): Colourless oil (15% yield):

Analysis calculated for C$_{21}$H$_{28}$N$_4$O$_3$S .0.8H$_2$O Requires C 58.53 H 6.92 N 13.00 Found C 58.41 H 6.57 N 12.88 i.r. (CDCl$_3$) 1600, 1330, 1155 cm$^{-1}$ delta$_H$ 8.42 (1H, dd, J 4.8, 1.3 Hz), 8.17–8.10 (2H, m), 7.85 (2H, d, J 8.3 Hz), 7.42 (2H, d, J 8.3 Hz), 7.29 (1H, dd, J 7.9, 4.8 Hz), 5.57 (2H, s), 4.81 (1H, d, J 8.6 Hz), 3.43–3.10 (5H, m), 1.60–1.19 (3H, m), 1.00 (3H, t, J 6.9 Hz), 0.79 (3H, d, J 6.6 Hz), 0.71 (3H, d, J 6.5 Hz).

Regioisomer (B): Colourless oil (15% yield):

Analysis calculated for C$_{21}$H$_{28}$N$_4$O$_3$S .0.8H$_2$O Requires C 58.53 H 6.92 N 13.00 Found C 58.63 H 6.57 N 13.02 i.r. (CDCl₃) 1610, 1330, 1150 cm⁻¹ delta$_H$ 8.52 (1H, dd, J 4.8, 1.4 Hz), 8.25 (1H, s), 7.80 (2H, d, J 8.3 Hz), 7.50 (1H, dd, J 8.2, 1.5 Hz), 7.24 (2H, d, J 8.3 Hz), 7.12 (1H, d, J 8.2, 4.8 Hz), 5.46 (2H, s), 5.33 (1H, d, J 8.5 Hz), 3.42–3.27 (1H, m), 3.29–3.08 (4H, m), 1.60–1.16 (3H, m), 0.95 (3H, t, J 6.9 Hz), 0.74 (3H, d, J 6.6 Hz), 0.67 (3H, d, J 6.5 Hz).

EXAMPLES 46–81

The compounds of Examples 46–81 may be prepared either by the procedure of Example 5 or by the procedure of Example 45 employing the appropriate heterocycle as starting material.

46. N-4-(1H-2-n-Propylpyrrolo[2,3-b]pyridinylmethyl) phenylsulphonylglycine methyl ester
47. N-4-(2H-3-n-Propylisoquinol-1-onylmethyl) phenylsulphonyl-2,2-dimethylglycine methyl ester
48. N-4-(3H-2-n-Butyl-5-methylthieno[2,3-d]pyrimidin-4-onylmethyl)phenylsulphonyl-1-methoxycarbonylcyclohexylamine
49. N-4-(3H-2-n-Butyl-6-methyl-5-phenylimidazo[1,2-b]-1,2,4-triazolylmethyl)phenylsulphonyl-D,L-alanine methyl ester
50. N-4-(1H-4-Chloro-2,6-dimethylpyrrolo[3,2-c]pyridinylmethyl)phenylsulphonyl-L-phenylalanine methyl ester
51. N-4-(1H-4-Chloro-2,6-dimethylpyrrolo[3,2-c]pyridinylmethyl)phenylsulphonyl-D-phenylalanine methyl ester
52. N-4-(7H-8-n-Butyl-3,7-dihydro-1,3-dimethylpurine-2,6-dionylmethyl)phenylsulphonyl-L-phenylalanine methyl ester
53. N-4-(7H-8-n-Butyl-3,7-dihydro-1,3-dimethylpurine-2,6-dionylmethyl)phenylsulphonyl-D-phenylalanine methyl ester
54. N-4-(1H-3,5-Dibutyl-1,2,4-triazolylmethyl) phenylsulphonyl-L-valine methyl ester
55. N-4-(1H-3,5-Dibutyl-1,2,4-triazolylmethyl) phenylsulphonyl-D-valine methyl ester
56. N-4-(3H-2-n-Butyl-6-(1-hydroxy-1-methylethyl) quinazolin-4-onylmethyl)phenylsulphonyl-D,L-t-butylglycine methyl ester
57. N-4-(7H-2,4-Dimethyl-5,7-dihydropyrrolo[2,3-d] pyrimidin-6-onylmethyl)phenylsulphonyl-L-leucine ethyl ester
58. N-4-(7H-2,4-Dimethyl-5,7-dihydropyrrolo[2,3-d] pyrimidin-6-onylmethyl)phenylsulphonyl-D-leucine ethyl ester
59. N-4-(1H-2-n-Propyl-4-chloro-5-formylimidazolylmethyl)phenylsulphonyl-L-isoleucine ethyl ester
60. N-4-(1H-2-n-Propyl-4-chloro-5-formylimidazolylmethyl)phenylsulphonyl-D-isoleucine ethyl ester
61. N-Methyl-N-4-(3H-2-ethyl-5,7-dimethylimidazo[4,5-b] pyridinylmethyl)phenylsulphonylglycine methyl ester
62. N-Methyl-N-4-(3H-2-ethyl-5,7-dimethylimidazo[4,5-b] pyridinylmethyl)phenylsulphonyl-2,2-dimethylglycine methyl ester
63. N-Methyl-N-4-(3H-2-ethyl-5,7-dimethylimidazo[4,5-b] pyridinylmethyl)phenylsulphonyl-1-methoxycarbonylcyclohexylamine
64. N-Methyl-N-4-(3H-2-ethyl-5,7-dimethylimidazo[4,5-b] pyridinylmethyl)phenylsulphonyl-D,L-alanine methyl ester
65. N-4-(3H-2-Ethyl-5,7-dimethylimidazo[4,5-b] pyridinylmethyl)phenylsulphonyl-D,L-alanine methyl ester
66. N-Methyl-N-4-(3H-2-ethyl-5,7-dimethylimidazo[4,5-b] pyridinylmethyl)phenylsulphonyl-D,L-alanine methyl ester
67. N-Methyl-N-4-(4H-3-ethylthio-1,2,4-benzothiadiazinedioxidemethyl)phenylsulphonyl-D-phenylalanine methyl ester
68. N-Methyl-N-4-(4H-3-ethylthio-1,2,4-benzothiadiazinedioxidemethyl)phenylsulphonyl-L-phenylalanine methyl ester
69. N-Methyl-N-4-(4H-3-n-butyl-5-(4-chlorobenzylthio)-1,2,4-triazolylmethyl)phenylsulphonyl-L-valine methyl ester
70. N-Methyl-N-4-(4H-3-n-butyl-5-(4-chlorobenzylthio)-1,2,4-triazolylmethyl)phenylsulphonyl-D-valine methyl ester
71. N-Methyl-N-4-(1H-2-n-butyl-4-chloro-1,6-dihydro-5-hydroxycarbonyl-6-methylpyrimidinylmethyl) phenylsulphonyl-D,L-t-butylglycine methyl ester
72. N-Methyl-N-4-(1H-2-n-butyl-4-trifluoromethyl-5-hydroxycarbonylimidazolylmethyl)phenylsulphonyl-D-leucine ethyl ester
73. N-Methyl-N-4-(1H-2-n-butyl-4-trifluoromethyl-5-hydroxycarbonylimidazolylmethyl)phenylsulphonyl-L-leucine ethyl ester
74. N-Methyl-N-4-(3H-2-ethylpyrimidin-4-onylmethyl) phenylsulphonyl-L-isoleucine ethyl ester
75. N-Methyl-N-4-(3H-2-ethylpyrimidin-4-onylmethyl) phenylsulphonyl-D-isoleucine ethyl ester
76. N-Methyl-N-4-(1H-2-n-propylpyrrolylmethyl) phenylsulphonyl-D,L-norleucine ethyl ester
77. N-Methyl-N-4-(3H-2-n-butyl-6-methylpyrido[2,3-d] pyrimidin-4-onylmethyl)phenylsulphonyl-O-methyl-L-tyrosine methyl ester
78. N-Methyl-N-4-(3H-2-n-butyl-6-methylpyrido[2,3-d] pyrimidin-4-onylmethyl)phenylsulphonyl-O-methyl-D-tyrosine methyl ester
79. N-Methyl-N-4-(1H-3-n-butyl-1,4-dihydo-4-thioxoquinolinylmethyl)phenylsulphonyl-O-benzyl-D,L-serine methyl ester
80. N-Methyl-N-4-(1H-2-n-butyl-4-chloro-5-(3-methyl-1,2,4-oxadiazol-5-yl)imidazolylmethyl)-phenylsulphonyl-D,L-methionine methyl ester
81. N-Methyl-N-4-(1H-2-n-butyl-4-spirocyclopentane-2-imidazoline-5-onylmethyl)phenylsulphonyl-D,L-aspartic acid diethyl ester

EXAMPLE 82

N-Methyl-N-4-(9H-2,6-dichloropurinylmethyl) phenylsulphonyl-L-leucine n-propyl ester

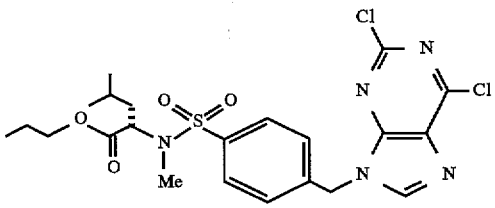

N-Methyl-N-4-(9H-2,6-dichloropurinylmethyl) phenylsulphonyl-L-leucine n-propyl ester was prepared by the procedure of Example 23 employing 2,6-dichloropurine in lieu of 2-butyl-4-chloro-5-hydroxymethylimidazole and N-methyl-N-4-bromomethylphenylsulphonyl-L-leucine n-propyl ester in lieu of N-methyl-N-4-bromomethylphenylsulphonyl-L-leucine ethyl ester.

Colourless viscous oil (24% yield after chromatography (silica: 0–2% methanol in DCM)):

i.r. (CHCl$_3$) 3680, 2960, 2870, 1730, 1595, 1565, 1350, 1170, 1150, 880 cm$^{-1}$ delta$_H$ 8.10 (1H, s), 7.82 (2H, d, J 8.3 Hz), 7.41 (2H, d, J 8.3 Hz), 5.49 (2H, s), 4.67 (1H, br t), 3.85 (2H, t, J 6.5 Hz), 2.83 (3H, s), 1.63–0.84 (14H, m);

delta$_C$ 170.94, 145.43, 138.64, 128.25, 128.12, 64.86, 57.25, 46.26, 38.12, 30.33, 29.79, 24.41, 22.99, 21.16, 18.96.

EXAMPLE 83

N-4-(1H-Imidazolylmethyl)phenylsulphonyl-L-leucinyl t-butyldiphenylsilyl ether

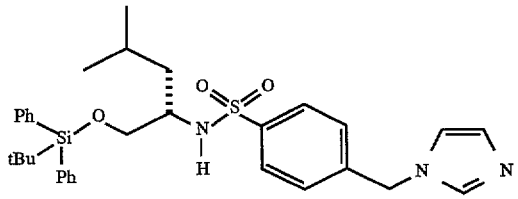

(a) N-4-Bromomethylphenylsulphonyl-L-leucinol

N-4-Bromomethylphenylsulphonyl-L-leucinol was prepared by the method of Example 1 Step (b) employing L-leucinol in lieu of L-leucine ethyl ester hydrochloride.

Colourless oil: (37% yield after chromatography (silica: 50% ethyl acetate in hexane).

delta$_H$ 7.91 (2H, d, J 8.3 Hz), 7.53 (2H, d, J 8.4 Hz), 5.31 (1H, d, J 7.7 Hz), 4.62 (2H, s), 3.62–3.44 (2H, m), 3.36–3.27 (1H, m), 2.60 (1H, br s), 1.45–1.37 (1H, m), 1.25 (2H, t, J 7.2 Hz), 0.76 (3H, d, J 6.5 Hz), 0.62 (3H, d, J 6.4 Hz).

(b) N-4-Bromomethylphenylsulphonyl-L-leucinyl 2-t-butyldiphenylsilyl ether 2-t-Butyldiphenylsilyl chloride (12.3 ml, 47.1 mmol) and 4-dimethylaminopyridine (10 mg) were added to a solution of N-4-bromomethylphenylsulphonyl-L-leucinol (15.0 g, 42.9 mmol) and diisopropylethylamine (37.3 ml, 0.21 mol) in dry DMF (150 ml) and the mixture stirred at room temperature under argon overnight. Ethyl acetate was added and the mixture washed with aqueous ammonium chloride and brine. The combined aqueous washings were extracted with ethyl acetate and the combined organics dried over anhydrous sodium sulphate, filtered and concentrated to give a quantitative yield of crude N-4-bromomethylphenylsulphonyl-L-leucinyl 2-t-butyldiphenylsilyl ether as a viscous oil which was used directly in the next step.

delta$_H$ 8.05–7.31 (14H, m), 4.89 (1H, d, J 10.0 Hz), 4.58 (2H, s), 3.51–3.42 (2H, m), 3.40–3.23 (1H, m), 1.78–1.69 (1H, m), 1.55–1.32 (2H, m), 1.02 (9H, s), 0.77 (3H, d, J 6.6 Hz), 0.72 (3H, d, J 6.5 Hz).

(c) N-4-(1H-Imidazolylmethyl)phenylsulphonyl-L-leucinyl t-butyldiphenylsilyl ether N-4-(1H-Imidazolylmethyl)phenylsulphonyl-L-leucinyl t-butyl-diphenylsilyl ether was prepared by the procedure of Example 1 Step (c) employing imidazole in lieu of 2-phenylimidazole and N-4-bromomethylphenylsulphonyl-L-leucinyl 2-t-butyldiphenylsilyl ether in lieu of N-4-bromomethylphenylsulphonyl-L-leucine ethyl ester.

Amorphous white solid (20% yield after chromatography (silica: 5% methanol in DCM)):

i.r. (CDCl$_3$) 3380, 2910, 1590, 1400 cm$^{-1}$ delta$_H$ 7.73 (2H, d, J 8.3 Hz), 7.60–7.47 (5H, m), 7.47–7.30 (6H, m), 7.14–7.04 (3H, m), 6.79 (1H, s), 5.52 (1H, d, J 8.2 Hz), 5.12 (2H, s), 3.57–3.41 (2H, m), 3.40–3.24 (1H, m), 1.55–1.36 (3H, m), 1.01 (9H, s), 0.77 (3H, d, J 6.1 Hz), 0.69 (3H, d, J 6.1 Hz).

EXAMPLE 84

N-4-(1H-Imidazolylmethyl)phenylsulphonyl-L-leucinol

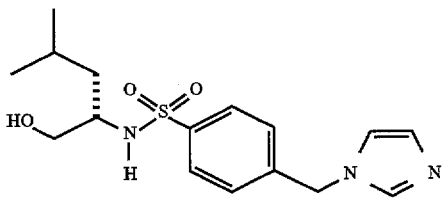

A stirred solution of N-4-(1H-imidazolylmethyl) phenylsulphonyl-L-leucinyl t-butyldiphenylsilyl ether (2.2 g, 3.82 mmol) in dry THF (50 ml) was treated at 0° C. with a 1M solution of tetrabutylammonium fluoride in THF (7.64 ml, 7.64 mmol). The reaction mixture was allowed to warm up to room temperature and was stirred for 5 h. The solvent was removed under reduced pressure and the residue purified by chromatography (silica: 5% methanol in DCM) to give N-4-(1H-imidazolylmethyl)phenylsulphonyl-L-leucinol (0.19 g, 15%) as a white amorphous solid.

Analysis calculated for C 16H$_{23}$N$_3$O$_3$S Requires C 56.95 H 6.87 N 12.45 Found C 57.00 H 6.92 N 12.54 i.r. (KBr) 1310, 1150, 1090 cm$^{-1}$ delta$_H$ 7.89 (2H, d, J 8.4 Hz), 7.58 (1H, br s), 7.28 (2H, d, J 8.3 Hz), 7.14 (1H, br s), 6.89 (1H, br s), 5.22 (2H, s), 4.71 (1H, d, J 7.8 Hz), 3.58 (1H, dd, J 11.0, 3.7 Hz), 3.47 (1H, dd, J 11.1, 4.8 Hz), 3.40–3.25 (1H, m), 1.53–1.20 (3H, m), 0.79 (3H, d, J 6.5 Hz), 0.66 (3H, d, J 6.4 Hz).

EXAMPLE 85

N-4-(1H-2-Methylimidazolylmethyl)phenylsulphonyl-L-leucinol

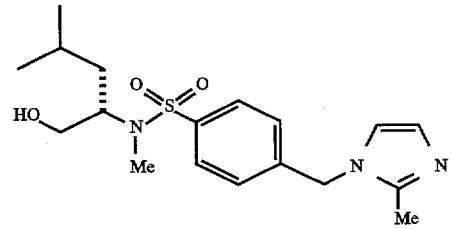

(a) N-Methy-N-4-bromomethylphenylsulphonyl-L-leucinyl 2-t-butyldiphenylsilyl ether N-Methy-N-4-bromomethylphenylsulphonyl-L-leucinyl 2-t-butyl-diphenylsilyl ether was prepared by the procedure of Example 2 Step (a) employing N-4-bromomethylphenylsulphonyl-L-leucinyl 2-t-butyldiphenylsilyl ether in lieu of N-4-bromomethylphenylsulphonyl-L-leucine ethyl ester.

delta$_H$ 7.75–7.33 (14H, m), 4.41 (2H, s), 3.76 (1H, m), 3.58–3.51 (2H, m), 2.77 (3H, s), 1.38–1.26 (1H, m), 1.05 (2H, m), 1.04 (9H, s), 0.86 (3H, d, J 5.9 Hz), 0.85 (3H, d, J 6.2 Hz).

(b) N-4-(1H-2-Methylimidazolylmethyl)phenylsulphonyl-L-leucinol

A suspension of potassium hydroxide (224 mg, 4.0 mmol), TDA-1 (4 drops) in dry acetonitrile (40 ml) was stirred for 10 min. at room temperature under argon. 2-Methylimidazole (137 mg, 1.67 mmol) was added and the reaction mixture was heated at 80° C. for 40 min. and cooled to 40° C. A solution of N-methyl-N-4-bromomethylphenylsulphonyl-L-leucinyl 2-t- butyldiphenylsilyl ether (1.0 g, 1.67 mmol) in dry acetonitrile (15 ml) was added and the reaction mixture stirred at 40° C. overnight and cooled to room temperature. Ethanol (50 ml) was added and the resulting slurry filtered through a short pad of celite. Column chromatography (silica: 5% methanol in DCM) gave the deprotected compound N-4-(1H-2-methhylimidazolylmethyl)phenylsulphonyl-L-leucinol (0.10 g, 17%) as a white crystalline solid: m.p. 157°–159° C.

Analysis calculated for $C_{18}H_{27}N_3O_3S.0.3H_2O$ Requires C 58.29 H 7.50 N 11.33 Found C 58.35 H 7.33 N 11.33 i.r. (CDCl$_3$) 3620, 2960, 1600, 1405, 1330, 1195 cm$^{-1}$ delta$_H$ 7.82 (2H, d, J 8.4 Hz), 7.13 (2H, d, J 8.2 Hz), 6.94 (1H, d, J 1.3 Hz), 6.84 (1H, d, J 1.3 Hz), 5.12 (2H, s), 4.07–4.01 (1H, m), 3.55–3.40 (2H, m), 2.73 (3H, s), 2.28 (3H, s), 1.46–1.38 (1H, m), 1.17 (2H, t, J 7.2 Hz), 0.83 (3H, d, J 6.5 Hz), 0.81 (3H, d, J 6.4 Hz).

EXAMPLE 86

N-Methyl-N-4-(1H-2-butyl-4-chloro-5-hydroxymethylimidazolylmethyl)phenylsulphonyl-L-leucine

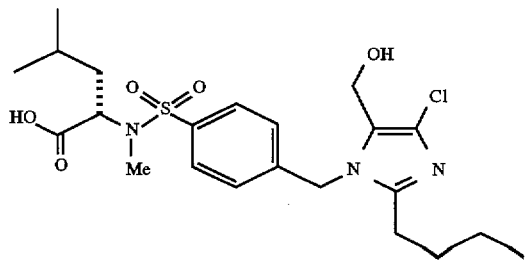

2M Potassium hydroxide (1.4 ml) was added to a solution of N-methyl-4-(1H-2-butyl-4-chloro-5-hydroxymethylimidazolylmethyl)phenylsulphonyl-L-leucine ethyl ester (280 mg, 0.54 mmol) in ethanol (25 ml). The reaction mixture was stirred at room temperature overnight. The solvent was removed under reduced pressure and water was added to the residue. The pH of the resulting solution was adjusted to pH 4 by the addition of 2M HCl. A white cloudy precipitate formed, which was extracted into ethyl acetate. The combined organic extracts were dried over anhydrous sodium sulphate, filtered and evaporated to give N-methyl-N-4-(1H-2-butyl-4-chloro-5-hydroxymethylimidazolylmethyl)phenylsulphonyl-L-leucine (92 mg, 35%) as a colourless oil i.r. (CDCl$_3$) 1740 cm$^{-1}$ delta$_H$ 8.55–8.00 (1H, br s), 7.82 (2H, d, J 8.3 Hz), 7.07 (2H, d, J 8.3 Hz), 5.19 (2H, s), 4.91 (2H, s), 4.74–4.63 (1H, m), 2.81 (3H, s), 2.55 (2H, t, J 7.5 Hz), 1.73–1.47 (5H, m), 1.38–1.19 (2H, m), 1.00–0.89 (6H, m), 0.84 (3H, t, J 7.2 Hz);

delta$_C$ 169.36, 147.93, 138.80, 137.79, 128.32, 126.88, 124.80, 119.30, 56.03, 52.76, 45.90, 36.65, 28.30, 25.00, 23.11, 21.73, 20.81, 19.63, 19.12, 12.22.

EXAMPLES 87 AND 88

The compounds of Examples 87 and 88 were prepared by the procedure of Example 86 employing the compounds of Examples 43 and 44 respectively in lieu of N-methyl-4-(1H-2-butyl-4-chloro-5-hydroxymethylimidazolylmethyl)phenylsulphonyl-L-leucine ethyl ester.

87. N-Methyl-N-4-(1H-2-ethylimidazolylmethyl)phenylsulphonyl-L-leucine

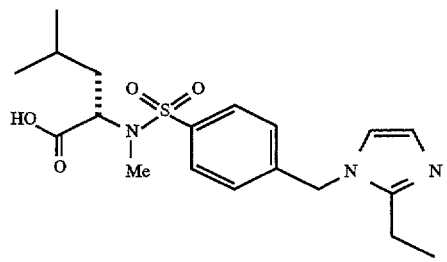

Amorphous solid (3% yield after chromatography (10% methanol in DCM)):

i.r. (CDCl$_3$) 3960, 1715, 1335, 1150 cm$^{-1}$ delta$_H$ 7.79 (2H, d, J 8.3 Hz), 7.35–7.32 (3H, m), 7.25 (1H, d, J 1.8 Hz), 5.38 (2H, s), 4.41 (1H, t, J 7.5 Hz), 2.84 (2H, q, J 7.5 Hz), 2.81 (3H, s), 1.59–1.49 (3H, m), 1.22 (3H, t, J 7.5 Hz), 0.87 (3H, d, J 6.2 Hz), 0.86 (3H, d, J 6.0 Hz);

delta$_C$ 177.14, 150.66, 141.04, 140.79, 129.26, 128.97, 123.08, 122.26, 60.55, 50.62, 39.67, 30.53, 25.89, 23.68, 21.76, 19.88, 11.78.

88. N-Methyl-N-4-(1H-2-n-propylimidazolylmethyl) phenylsulphonyl-L-leucine

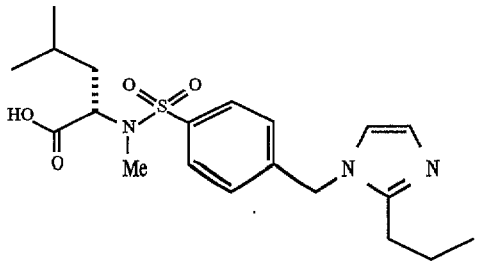

Yellow oil (3% yield after chromatography (10% methanol in DCM)):

i.r. (CDCl$_3$) 3630, 3350, 2960, 2200, 1715, 1330 cm$^{-1}$ delta$_H$ 7.79 (2H, d, J 8.3 Hz), 7.29 (2H, d, J 8.3 Hz), 7.21 (1H, d, J 1.8 Hz), 7.13 (1H, d, J 1.6 Hz), 5.34 (2H, s), 4.51–4.45 (1H, m), 2.81 (3H, s), 2.73 (3H, t, J 7.7 Hz), 1.68–1.50 (3H, m), 0.93–0.87 (9H, m);

delta$_C$ 176.54, 149.67, 141.79, 140.62, 129.17, 128.63, 124.06, 122.51, 59.97, 54.79, 39.76, 30.29, 28.38, 25.83, 23.56, 21.94, 21.62, 13.88.

EXAMPLES 89–162

The compounds of Examples 89–162 may be prepared by the procedure of Example 86 employing the appropriate ester as starting material in lieu of N-methyl-4-(1H-2-butyl-4-chloro-5-hydroxymethylimidazolylmethyl) phenylsulphonyl-L-leucine ethyl ester.

89. N-4-(1H-2-Butyl-4-chloro-5-hydroxymethylimidazolylmethyl) phenylsulphonylglycine 90. N-4-(1H-2-Butyl-4-chloro-5-hydroxymethylimidazolylmethyl)phenylsulphonyl-2,2-dimethylglycine 91. N-4-(1H-2-Butyl-4-chloro-5-hydroxymethylimidazolylmethyl)phenylsulphonyl-1-aminocyclohexanecarboxylic acid 92. N-4-(1H-2-Butyl-4-chloro-5-hydroxymethylimidazolylmethyl)phenylsulphonyl-D,L-alanine 93. N-4-(1H-2-Butyl-4-chloro-5-hydroxymethylimidazolylmethyl)phenylsulphonyl-D-phenylalanine
94. N-4-(1H-2-Butyl-4-chloro-5-hydroxymethylimidazolylmethyl)phenylsulphonyl-L-phenylalanine
95. N-4-(1H-2-Butyl-4-chloro-5-hydroxymethylimidazolylmethyl)phenylsulphonyl-L-valine
96. N-4-(1H-2-Butyl-4-chloro-5-hydroxymethylimidazolylmethyl)phenylsulphonyl-D-valine
97. N-4-(1H-2-Butyl-4-chloro-5-hydroxymethylimidazolylmethyl)phenylsulphonyl-D,L-t-butylglycine
98. N-4-(1H-2-Butyl-4-chloro-5-hydroxymethylimidazolylmethyl)phenylsulphonyl-D-leucine
99. N-4-(1H-2-Butyl-4-chloro-5-hydroxymethylimidazolylmethyl)phenylsulphonyl-D-leucine
100. N-4-(1H-2-Butyl-4-chloro-5-hydroxymethylimidazolylmethyl)phenylsulphonyl-L-isoleucine
101. N-4-(1H-2-Butyl-4-chloro-5-hydroxymethylimidazolylmethyl)phenylsulphonyl-D-isoleucine
102. N-4-(1H-2-Butyl-4-chloro-5-hydroxymethylimidazolylmethyl)phenylsulphonyl-D,L-norleucine
103. N-4-(1H-2-Butyl-4-chloro-5-hydroxymethylimidazolylmethyl)phenylsulphonyl-O-methyl-L-tyrosine
104. N-4-(1H-2-Butyl-4-chloro-5-hydroxymethylimidazolylmethyl)phenylsulphonyl-O-methyl-D-tyrosine
105. N-4-(1H-2-Butyl-4-chloro-5-hydroxymethylimidazolylmethyl)phenylsulphonyl-O-benzyl-D,L-serine
106. N-4-(1H-2-Butyl-4-chloro-5-hydroxymethylimidazolylmethyl)phenylsulphonyl-D,L-methionine
107. N-4-(1H-2-Butyl-4-chloro-5-hydroxymethylimidazolylmethyl)phenylsulphonyl-D,L-aspartic acid
108. N-Methyl-N-4-(1H-2-butyl-4-chloro-5-hydroxymethylimidazolylmethyl)phenylsulphonylglycine
109. N-Methyl-N-4-(1H-2-butyl-4-chloro-5-hydroxymethylimidazolylmethyl)phenylsulphonyl-2,2-dimethylglycine
110. N-Methyl-N-4-(1H-2-butyl-4-chloro-5-hydroxymethylimidazolylmethyl)phenylsulphonyl-1-aminocyclohexanecarboxylic acid
111. N-Methyl-N-4-(1H-2-butyl-4-chloro-5-hydroxymethylimidazolylmethyl)phenylsulphonyl-D,L-alanine
112. N-Ethyl-N-4-(1H-2-butyl-4-chloro-5-hydroxymethylimidazolylmethyl)phenylsulphonyl-D-phenylalanine
113. N-Ethyl-N-4-(1H-2-butyl-4-chloro-5-hydroxymethylimidazolylmethyl)phenylsulphonyl-L-phenylalanine
114. N-Methyl-N-4-(1H-2-butyl-4-chloro-5-hydroxymethylimidazolylmethyl)phenylsulphonyl-L-valine
115. N-Methyl-N-4-(1H-2-butyl-4-chloro-5-hydroxymethylimidazolylmethyl)phenylsulphonyl-D-valine
116. N-Methyl-N-4-(1H-2-butyl-4-chloro-5-hydroxymethylimidazolylmethyl)phenylsulphonyl-D,L-t-butylglycine
117. N-Methyl-N-4-(1H-2-butyl-4-chloro-5-hydroxymethylimidazolylmethyl)phenylsulphonyl-L-leucine
118. N-Methyl-N-4-(1H-2-butyl-4-chloro-5-hydroxymethylimidazolylmethyl)phenylsulphonyl-D-leucine
119. N-n-Propyl-N-4-(1H-2-butyl-4-chloro-5-hydroxymethylimidazolylmethyl)phenylsulphonyl-L-isoleucine
120. Non-Propyl-N-4-(1H-2-butyl-4-chloro-5-hydroxymethylimidazolylmethyl)phenylsulphonyl-D-isoleucine
121. N-Methyl-N-4-(1H-2-butyl-4-chloro-5-hydroxymethylimidazolylmethyl)phenylsulphonyl-D,L-norleucine
122. N-Methyl-N-4-(1H-2-butyl-4-chloro-5-hydroxymethylimidazolylmethyl)phenylsulphonyl-O-methyl-L-tyrosine
123. N-Methyl-N-4-(1H-2-butyl-4-chloro-5-hydroxymethylimidazolylmethyl)phenylsulphonyl-O-methyl-D-tyrosine
124. N-Methyl-N-4-(1H-2-butyl-4-chloro-5-hydroxymethylimidazolylmethyl)phenylsulphonyl-O-benzyl-D,L-serine
125. N-Methyl-N-4-(1H-2-butyl-4-chloro-5-hydroxymethylimidazolylmethyl)phenylsulphonyl-D,L-methionine
126. N-Methyl-N-4-(1H-2-butyl-4-chloro-5-hydroxymethylimidazolylmethyl)phenylsulphonyl-D,L-aspartic acid
127. N-4-(1H-2-n-Propylpyrrolo[2,3-b]pyridinylmethyl)phenylsulphonylglycine
128. N-4-(2H-3-n-Propylisoquinol-1-onylmethyl)phenylsulphonyl-2,2-dimethylglycine
129. N-4-(3H-2-n-Butyl-5-methylthieno[2,3-d]pyrimidin-4-onylmethyl)phenylsulphonyl-1-aminocyclohexanecarboxylic acid
130. N-4-(3H-2-n-Butyl-6-methyl-5-phenylimidazo[1,2-b]-1,2,4-triazolylmethyl)phenylsulphonyl-D,L-alanine
131. N-4-(1H-4-Chloro-2,6-dimethylpyrrolo[3,2-c]pyridinylmethyl)phenylsulphonyl-L-phenylalanine
132. N-4-(1H-4-Chloro-2,6-dimethylpyrrolo[3,2-c]pyridinylmethyl)phenylsulphonyl-D-phenylalanine
133. N-4-(7H-8-n-Butyl-3,7-dihydro-1,3-dimethylpurine-2,6-dionylmethyl)phenylsulphonyl-L-phenylalanine
134. N-4-(7H-8-n-Butyl-3,7-dihydro-1,3-dimethylpurine-2,6-dionylmethyl)phenylsulphonyl-D-phenylalanine
135. N-4-(1H-3,5-Dibutyl-1,2,4-triazolylmethyl)phenylsulphonyl-L-valine
136. N-4-(1H-3,5-Dibutyl-1,2,4-triazolylmethyl)phenylsulphonyl-D-valine
137. N-4-(3H-2-n-Butyl-6-(1-hydroxy-1-methylethyl)quinazolin-4-onylmethyl)phenylsulphonyl-D,L-t-butylglycine
138. N-4-(7H-2,4-Dimethyl-5,7-dihydropyrrolo[2,3-d]pyrimidin-6-onylmethyl)phenylsulphonyl-L-leucine
139. N-4-(7H-2,4-Dimethyl-5,7-dihydropyrrolo[2,3-d]pyrimidin-6-onylmethyl)phenylsulphonyl-D-leucine
140. N-4-(1H-2-n-Propyl-4-chloro-5-formylimidazolylmethyl)phenylsulphonyl-L-isoleucine
141. No4-(1H-2-n-Propyl-4-chloro-5-formylimidazolylmethyl)phenylsulphonyl-D-isoleucine
142. N-Methyl-N-4-(3H-2-ethyl-5,7-dimethylimidazo[4,5-b]pyridinylmethyl)phenylsulphonylglycine 143. N-Methyl-N-4-(3H-2-ethyl-5,7-dimethylimidazo[4,5-b]pyridinylmethyl)phenylsulphonyl-2,2-dimethylglycine
144. N-Methyl-N-4-(3H-2-ethyl-5,7-dimethylimidazo[4,5-b]pyridinylmethyl)phenylsulphonyl-1-aminocyclohexanecarboxylic acid
145. N-Methyl-N-4-(3H-2-ethyl-5,7-dimethylimidazo[4,5-b]pyridinylmethyl)phenylsulphonyl-D,L-alanine
146. N-4-(3H-2-Ethyl-5,7-dimethylimidazo[4,5-b]pyridinylmethyl)phenylsulphonyl-D,L-alanine
147. N-Methyl-N-4-(3H-2-ethyl-5,7-dimethylimidazo[4,5-b]pyridinylmethyl)phenylsulphonyl-D,L-alanine
148. N-Methyl-N-4-(4H-3-ethylthio-1,2,4-benzothiadiazinedioxidemethyl)phenylsulphonyl-D-phenylalanine
149. N-Methyl-N-4-(4H-3-ethylthio-1,2,4-benzothiadiazinedioxidemethyl)phenylsulphonyl-L-phenylalanine
150. N-Methyl-N-4-(4H-3-n-butyl-5-(4-chlorobenzylthio)-1,2,4-triazolylmethyl)phenylsulphonyl-L-valine
151. N-Methyl-N-4-(4H-3-n-butyl-5-(4-chlorobenzylthio)-1,2,4-triazolylmethyl)phenylsulphonyl-D-valine
152. N-Methyl-N-4-(1H-2-n-butyl-4-chloro-1,6-dihydro-5-hydroxycarbonyl-6-methylpyrimidinylmethyl)phenylsulphonyl-D,L-t-butylglycine
153. N-Methyl-N-4-(1H-2-n-butyl-4-trifluoromethyl-5-hydroxycarbonylimidazolylmethyl)phenylsulphonyl-D-leucine
154. N-Methyl-N-4-(1H-2-n-butyl-4-trifluoromethyl-5-hydroxycarbonylimidazolylmethyl)phenylsulphonyl-L-leucine
155. N-Methyl-N-4-(3H-2-ethylpyrimidin-4-onylmethyl)phenylsulphonyl-L-isoleucine
156. N-Methyl-N-4-(3H-2-ethylpyrimidin-4-onylmethyl)phenylsulphonyl-D-isoleucine
157. N-Methyl-N-4-(1H-2-n-propylpyrrolylmethyl)phenylsulphonyl-D,L-norleucine
158. N-Methyl-N-4-(3H-2-n-butyl-6-methylpyrido[2,3-d]pyrimidin-4-onylmethyl)phenylsulphonyl-O-methyl-L-tyrosine
159. N-Methyl-N-4-(3H-2-n-butyl-6-methylpyrido[2,3-d]pyrimidin-4-onylmethyl)phenylsulphonyl-O-methyl-D-tyrosine
160. N-Methyl-N-4-(1H-3-n-butyl-1,4-dihydo-4-thioxoquinolinylmethyl)phenylsulphonyl-O-benzyl-D,L-serine
161. N-Methyl-N-4-(1H-2-n-butyl-4-chloro-5-(3-methyl-1,2,4-oxadiazol-5-yl)imidazolylmethyl)-phenylsulphonyl-D,L-methionine
162. N-Methyl-N-4-(1H-2-n-butyl-4-spirocyclopentane-2-imidazoline-5-onylmethyl)phenylsulphonyl-D,L-aspartic acid

EXAMPLES 163–176

The carboxylic acid derivatives of Examples 89–162 may be converted to the corresponding tetrazoles by standard literature protocols such as that described by J. V. Duncia, M. E. Pierce and J. B. Santella III, J. Org. Chem., 1991, 56, 2395–2400.

163. N-4-(1H-2-Butyl-4-chloro-5-hydroxymethylimidazolylmethyl)phenylsulphonyl-1-(1H-tetrazol-5-yl)methylamine
164. N-Methyl-N-4-(1H-2-butyl-4-chloro-5-hydroxymethylimidazolylmethyl)phenylsulphonyl-1-methyl-1-(1H-tetrazol-5-yl)ethylamine
165. N-Methyl-N-4-(1H-2-butyl-4-chloro-5-hydroxymethylimidazolylmethyl)phenylsulphonyl-1-(1H-tetrazol-5-yl)cyclohexylamine
166. (S)-N-4-(1H-3,5-Dibutyl-1,2,4-triazolylmethyl)phenylsulphonyl-2-methyl-1-(1H-tetrazol-5-yl)propylamine
167. (R)-N-4-(1H-3,5-Dibutyl-1,2,4-triazolylmethyl)phenylsulphonyl-2-methyl-1-(1H-tetrazol-5-yl)propylamine
168. (S)-N-4-(1H-2-Butyl-4-chloro-5-formylimidazolylmethyl)phenylsulphonyl-2-methyl-1-(1H-tetrazol-5-yl)butylamine
169. (R)-N-4-(1H-2-Butyl-4-chloro-5-formylimidazolylmethyl)phenylsulphonyl-2-methyl-1-(1H-tetrazol-5-yl)butylamine
170. N-Methyl-N-4-(1H-2-n-butyl-4-chloro-1,6-dihydro-5-hydroxycarbonyl-6-methylpyrimidinylmethyl)phenylsulphonyl-2,2-dimethyl-1-(1H-tetrazol-5-yl)propylamine
171. N-Methyl-N-4-(1H-2-butyl-4-chloro-5-hydroxymethylimidazolylmethyl)phenylsulphonyl-1-(1H-tetrazol-5-yl)ethylamine
172. (S)-N-Ethyl-N-4-(1H-2-butyl-4-chloro-5-hydroxymethylimidazolylmethyl)phenylsulphonyl-1-phenyl-1-(1H-tetrazol-5-yl)methylamine
173. (R)-N-Ethyl-N-4-(1H-2-butyl-4-chloro-5-hydroxymethylimidazolylmethyl)phenylsulphonyl-1-phenyl-1-(1H-tetrazol-5-yl)methylamine
174. (S)-N-Methyl-N-4-(1H-2-butyl-4-chloro-5-hydroxymethylimidazolylmethyl)phenylsulphonyl-1-methyl-1-(1H-tetrazol-5-yl)ethylamine
175. (R)-N-Methyl-N-4-(1H-2-butyl-4-chloro-5-hydroxymethylimidazolylmethyl)phenylsulphonyl-1-methyl-1-(1H-tetrazol-5-yl)ethylamine
176. N-Methyl-N-4-(1H-2-butyl-4-chloro-5-hydroxymethylimidazolylmethyl)phenylsulphonyl-2,2-dimethyl-1-(1H-tetrazol-5-yl)propylamine

EXAMPLES 177–203

The carboxylic acid derivatives of Examples 89–162 may be converted to the corresponding amide derivatives by standard literature protocols.

177. N-4-(1H-2-Butyl-4-chloro-5-hydroxymethylimidazolylmethyl)phenylsulphonylglycine 1H-tetrazol-5-ylamide
178. N-4-(1H-2-Butyl-4-chloro-5-hydroxymethylimidazolylmethyl)phenylsulphonyl-2,2-dimethylglycine 1H-tetrazol-5-ylamide.
179. N-4-(1H-2-Butyl-4-chloro-5-hydroxymethylimidazolylmethyl)phenylsulphonyl-D,L-alanine 1H-tetrazol-5-ylamide
180. N-4-(1H-2-Butyl-4-chloro-5-hydroxymethylimidazolylmethyl)phenylsulphonyl-D-phenylalanine 1H-tetrazol-5-ylamide
181. N-4-(1H-2-Butyl-4-chloro-5-hydroxymethylimidazolylmethyl)phenylsulphonyl-L-phenylalanine 1H-tetrazol-5-ylamide
182. N-4-(1H-2-Butyl-4-chloro-5-hydroxymethylimidazolylmethyl)phenylsulphonyl-L-valine trifluoromethylsulphonylamide
183. N-4-(1H-2-Butyl-4-chloro-5-hydroxymethylimidazolylmethyl)phenylsulphonyl-D-valine trifluoromethylsulphonylamide
184. N-4-(1H-2-Butyl-4-chloro-5-hydroxymethylimidazolylmethyl)phenylsulphonyl-D,L-t-butylglycine 1H-tetrazol-5-ylamide
185. N-4-(1H-2-Butyl-4-chloro-5-hydroxymethylimidazolylmethyl)phenylsulphonyl-D-leucine methylsulphonylamide
186. N-4-(1H-2-Butyl-4-chloro-5-hydroxymethylimidazolylmethyl)phenylsulphonyl-D-leucine methylsulphonylamide 187. N-Methyl-N-4-(3H-2-ethyl-5,7-dimethylimidazo[4,5-b]pyridinylmethyl)phenylsulphonylglycine 1H-tetrazol-5-ylamide
188. N-Methyl-N-4-(3H-2-ethyl-5,7-dimethylimidazo[4,5-b]pyridinylmethyl)phenylsulphonyl-2,2-dimethylglycine 1H-tetrazol-5-ylamide
189. N-Methyl-N-4-(3H-2-ethyl-5,7-dimethylimidazo[4,5-b]pyridinylmethyl)phenylsulphonyl-D,L-alanine 1H-tetrazol-5-ylamide
190. N-4-(3H-2-Ethyl-5,7-dimethylimidazo[4,5-b]pyridinylmethyl)phenylsulphonyl-D,L-alanine 1H-tetrazol-5-ylamide
191. N-Methyl-N-4-(3H-2-ethyl-5,7-dimethylimidazo[4,5-b]pyridinylmethyl)phenylsulphonyl-D,L-alanine 1H-tetrazol-5-ylamide
192. N-Methyl-N-4-(4H-3-ethylthio-1,2,4-benzothiadiazinedioxidemethyl)phenylsulphonyl-D-phenylalanine trifluoromethylsulphonylamide
193. N-Methyl-N-4-(4H-3-ethylthio-1,2,4-benzothiadiazinedioxidemethyl)phenylsulphonyl-L-phenylalanine trifluoromethylsulphonylamide
194. N-Methyl-N-4-(1H-2-butyl-4-chloro-5-hydroxymethylimidazolylmethyl)phenylsulphonylglycine 1H-tetrazol-5-ylamide
195. N-Methyl-N-4-(1H-2-butyl-4-chloro-5-hydroxymethylimidazolylmethyl)phenylsulphonyl-2,2-dimethylglycine 1H-tetrazol-5-ylamide
196. N-Methyl-N-4-(1H-2-butyl-4-chloro-5-hydroxymethylimidazolylmethyl)phenylsulphonyl-D,L-alanine 1H-tetrazol-5-ylamide
197. N-Ethyl-N-4-(1H-2-butyl-4-chloro-5-hydroxymethylimidazolylmethyl)phenylsulphonyl-D-phenylalanine 1H-tetrazol-5-ylamide
198. N-Ethyl-N-4-(1H-2-butyl-4-chloro-5-hydroxymethylimidazolylmethyl)phenylsulphonyl-L-phenylalanine 1H-tetrazol-5-ylamide
199. N-Methyl-N-4-(1H-2-butyl-4-chloro-5-hydroxymethylimidazolylmethyl)phenylsulphonyl-L-valine trifluoromethylsulphonylamide
200. N-Methyl-N-4-(1H-2-butyl-4-chloro-5-hydroxymethylimidazolylmethyl)phenylsulphonyl-D-valine trifluoromethylsulphonylamide
201. N-Methyl-N-4-(1H-2-butyl-4-chloro-5-hydroxymethylimidazolylmethyl)phenylsulphonyl-D,L-t-butylglycine trifluoromethylsulphonylamide
202. N-Methyl-N-4-(1H-2-butyl-4-chloro-5-hydroxymethylimidazolylmethyl)phenylsulphonyl-L-leucine 1H-tetrazol-5-ylamide
203. N-Methyl-N-4-(1H-2-butyl-4-chloro-5-hydroxymethylimidazolylmethyl)phenylsulphonyl-D-leucine 1H-tetrazol-5-ylamide EXAMPLE 204
Inhibition of [$^3$H]-PAF Receptor Binding The inhibition of [$^3$H]-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgCl$_2$, pH 7.0, 0.25% BSA) to make the final volume 1 ml. Incubation was initiated by the addition of 100 µg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

% Inhibition=[(TB−TBA)/SB]×100 where the specific binding SB=TB−NSB

Table 1 lists results from this assay for inhibition of [$^3$H]-PAF receptor binding for illustrative examples of the compounds of this invention.

TABLE 1

| Results for inhibition of [$^3$H]-PAF receptor binding | |
|---|---|
| Example | Inhibition of [$^3$H]-PAF binding IC$_{50}$ nM |
| 1 | 7 |
| 4 | 5 |

TABLE 1-continued

Results for inhibition of [$^3$H]-PAF receptor binding

| Example | Inhibition of [$^3$H]-PAF binding IC$_{50}$ nM |
|---|---|
| 43 | 5 |
| 45A | 20 |

EXAMPLE 205
Inhibition of Angiotensin II Induced Contraction of Rabbit Aorta The angiotensin II receptor antagonist activity of the compounds of general formula I is demonstrated in vitro by their ability to inhibit the contraction of rabbit aorta rings caused by angiotensin II. Male New Zealand White rabbits (2.0–2.5 kg) were killed with an overdose of anaesthetic (sodium pentobarbitone, 60 mg/kg) followed by exsanguination. The thoracic aorta was removed and cut into rings 2–3 mm wide. The endothelium was removed by immersion of the rings in 3% deoxycholate. The rings were mounted in a 25 ml organ bath under a 3 g resting tension. Dose response curves to angiotensin II were determined in the presence and absence of antagonists. Illustrative results from this assay for the inhibition of angiotensin II induced contraction of rabbit aorta rings are shown in FIG. 1.

We claim:
1. A compound of general formula I:

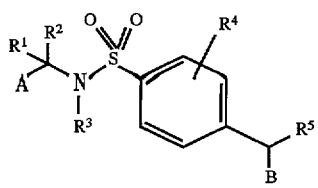

wherein:
A represents:

a) a —VR$^6$ group wherein V is —C(=O)—, —C(=O)O—, —CH$_2$O—, —CH$_2$OC(=O)—, —C(=S)—, —CH$_2$OC(=O)NH—, —C(=S)O—, —CH$_2$S—, —C(=O)NHSO$_2$—, —SO$_2$NHC(=O)— or —CH$_2$OSiPh$_2$—; and R$^6$ is hydrogen, —C$_1$–C$_{18}$ alkyl, —C$_2$–C$_{18}$ alkenyl, —C$_2$–C$_{18}$ alkynyl, —(C$_1$–C$_6$ alkyl)OC$_1$–C$_6$ alkyl, —(C$_1$–C$_6$ alkyl)SC$_1$–C$_6$ alkyl, —(C$_1$–C$_6$ alkyl)O (C$_1$–C$_6$ alkyl)OC$_1$–C$_6$ alkyl, —C$_3$–C$_8$ cycloalkyl, —C$_4$–C$_8$ cycloalkenyl or pyridyl, (any of which may optionally be substituted with one or more substituents selected from halogen, hydroxyl, nitro, nitrile or carboxyl), C$_1$–C$_4$ perfluoroalkyl, a group —D or a —(C$_1$–C$_6$ alkyl)OD group wherein D represents a group

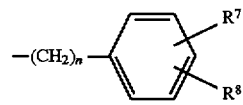

wherein n is an integer from 0 to 3, and each of R$^7$ and R$^8$ is independently hydrogen, —C$_1$–C$_6$ alkyl, —C$_2$–C$_6$ alkenyl, —C$_2$–C$_6$ alkynyl, halogen, —CN, —CO$_2$H, —CO$_2$C$_1$–C$_6$ alkyl, —CONH$_2$, —CONHC$_1$–C$_6$ alkyl, —CON(C$_1$–C$_6$ alkyl)$_2$, —CHO, —CH$_2$OH, —CF$_3$, —OC$_1$–C$_6$ alkyl, —SC$_1$–C$_6$ alkyl, —SOC$_1$–C$_6$ alkyl, —SO$_2$C$_1$–C$_6$ alkyl, —NH$_2$ or —NHCOMe;

b) a group —CH$_2$OSi(R$^6$)$_3$ wherein R$^6$ is as defined above; or c) tetrazolyl;

R$^1$ and R$^2$ each independently represent hydrogen, halogen, —C$_1$–C$_6$ alkyl optionally substituted by one or more halogen atoms, —C$_2$–C$_6$ alkenyl, —C$_2$–C$_6$ alkynyl, —(C$_1$–C$_6$ alkyl)CO$_2$C$_1$–C$_6$ alkyl, —(C$_1$–C$_6$ alkyl)SC$_1$–C$_6$ alkyl, —(C$_1$–C$_6$ alkyl) OC$_1$–C$_6$ alkyl, —(C$_1$–C$_6$ alkyl)N(C$_1$–C$_6$ alkyl)$_2$, —C$_3$–C$_8$ cycloalkyl, —C$_4$–C$_8$ cycloalkenyl, —(C$_1$–C$_6$ alkyl)C$_3$–C$_8$ cycloalkyl, —(C$_1$–C$_6$ alkyl) C$_4$–C$_8$ cycloalkenyl, —(C$_1$–C$_6$ alkyl)OC$_3$–C$_8$ cycloalkyl, —(C$_1$–C$_6$ alkyl)OC$_4$–C$_8$ cycloalkenyl, —(C$_1$–C$_6$ alkyl)SC$_3$–C$_8$ cycloalkyl, —(C$_1$–C$_6$ alkyl) SC$_4$–C$_8$ cycloalkenyl, a side chain of a naturally occurring amino acid, a group —D, or a —(C$_1$–C$_6$ alkyl)OD group wherein D is as defined above;

or R$^1$ and R$^2$ together with the carbon atom to which they are attached form a C$_3$–C$_8$ cycloalkyl ring;

R$^3$ represents hydrogen, —C$_1$–C$_6$ alkyl, —C$_2$–C$_6$ alkenyl, —C$_2$–C$_6$ alkynyl, —COC$_1$–C$_6$ alkyl, —CO$_2$C$_1$–C$_6$ alkyl, —(COC$_1$–C$_6$ alkyl)phenyl, —(CO$_2$C$_1$–C$_6$ alkyl)phenyl, —(C$_1$–C$_6$ alkyl) OC$_1$–C$_6$ alkyl, —(C$_1$–C$_6$ alkyl)SC$_1$–C$_6$ alkyl, —(C$_1$–C$_6$ alkyl)CO$_2$C$_1$–C$_6$ alkyl, —C$_3$–C$_8$ cycloalkyl, —C$_4$–C$_8$ cycloalkenyl or a group —D wherein D is as defined above;

or R$^1$ together with R$^3$ and the atoms to which they are attached form a 5 to 8 membered nitrogen-containing heterocyclic ring;

R$^4$ represents hydrogen, —C$_1$–C$_6$ alkyl, —C$_2$–C$_6$ alkenyl, halogen, —OC$_1$–C$_6$ alkyl, —C$_1$–C$_4$ perfluoroalkyl or —C$_3$–C$_8$ cycloalkyl;

R$^5$ represents hydrogen, —C$_1$–C$_6$ alkyl, —C$_2$–C$_6$ alkenyl, —C$_2$–C$_6$ alkynyl, —CO$_2$C$_1$–C$_6$ alkyl, —SC$_1$–C$_6$ alkyl, —(C$_1$–C$_6$ alkyl)SC$_1$–C$_6$ alkyl, —(C$_1$–C$_6$ alkyl)OC$_1$–C$_6$ alkyl, —(C$_1$–C$_6$ alkyl) phenyl or thiophenyl;

B represents imidazolyl, pyrido [4, 5-b] imidazolyl, pyrido [2, 3-b] pyrrolyl, isoquinolyl, thieno [2, 3-d] pyrimidinyl, pyrido [3, 2-c] pyrrolyl, purinyl, triazolyl, quinazolyl, pyrimidino [2, 3-d] dihydropyrrolyl, benzodioxothiadiazinyl, imidazo [1, 2-b] triazolyl, pyrimidinyl, pyrrolyl, pyrido [2, 3-d] pyrimidinyl or quinolinyl group, any of the rings of which groups may be optionally substituted with one or more substituents selected from hydrogen, halogen, —C$_1$–C$_4$ perfluoroalkyl, hydroxyl, carbonyl, thiocarbonyl, formyl, carboxyl, —CONH$_2$, —NO$_2$, a group —D wherein D is as defined above, —R$^{11}$, —OR$^{11}$, —SR$^{11}$, —SOR$^{11}$, —SO$_2$R$^{11}$, —NHR$^{11}$, —NR$^{11}$R$^{11}$, —CO$_2$R$^{11}$ or CONHR$^{11}$ wherein R$^{11}$ is —C$_1$–C$_6$ alkyl, —C$_2$–C$_6$ alkenyl, —C$_2$–C$_6$ alkynl, —C$_3$–C$_8$ cycloalkyl or C$_4$–C$_8$ cycloalkenyl, each of which is optionally substituted with one or more substituents selected from halogen, hydroxyl, amino, carboxyl, —C$_1$–C$_4$ perfluoroalkyl, —C$_1$–C$_6$ alkyl, —C$_2$–C$_6$ alkenyl, —C$_2$–C$_6$ alkynl, —C$_3$–C$_8$ cycloalkyl, C$_4$–C$_8$ cycloalkenyl, —OC$_1$–C$_6$ alkyl, —SC$_1$–C$_6$ alkyl, tetrazol-5-yl, a group —D wherein D is as defined above or a heteroaryl or heteroarylmethyl group;

or a pharmaceutically or veterinarily acceptable acid addition salt or hydrate thereof.

2. A compound as claimed in claim 1, in which A represents a) a VR$^6$ group wherein V is a —C(=O)O, —CH$_2$O—, —CH$_2$OSiPh$_2$— or —C(=O)NHSO$_2$— group and R$^6$ is as defined in claim 1, or B) a tetrazolyl group.

3. A compound as claimed in claim 2, wherein R$^6$ represents a hydrogen atom, a —C$_1$–C$_6$ alkyl group or a —C$_1$–C$_4$ perfluoroalkyl group.

4. A compound as claimed in claim 1, wherein $R^1$ represents a hydrogen atom, a —$C_1$–$C_6$ alkyl group, a —($C_1$–$C_6$ alkyl)$CO_2C_1$–$C_6$ alkyl group, a —($C_1$–$C_6$ alkyl)$SC_1$–$C_6$ alkyl group, the side chain of a naturally occurring amino acid, a group —D or a —($C_1$–$C_6$ alkyl)OD group, wherein n represents an integer of 0 or 1, $R^7$ represents a hydrogen atom or a —$OC_1$–$C_6$ alkyl group and $R^8$ represents a hydrogen atom.

5. A compound as claimed in claim 1, wherein $R^2$ represents a hydrogen atom or a —$C_1$–$C_6$ alkyl group, or together with $R^1$ and the carbon atom to which they are attached forms a $C_3$–$C_8$ cycloalkyl ring.

6. A compound as claimed in claim 1, wherein $R^3$ represents a hydrogen atom or a —$C_1$–$C_6$ alkyl group.

7. A compound as claimed in claim 1, wherein $R^4$ represents a hydrogen atom.

8. A compound as claimed in claim 1, wherein $R^5$ represents a hydrogen atom.

9. A compound as claimed in claim 1, wherein A represents the side chain of the amino acid leucine and $R^2$ is a hydrogen atom.

10. A compound as claimed in claim 1, wherein A represents a —C(=O)OH group, a —C(=O)$NHSO_2C_1$–$C_6$ alkyl group, a —C(=O)$NHSO_2C_1$–$C_4$ perfluoroalkyl group, a tetrazolyl group or a —C(=O)NH tetrazolyl group.

11. N-4-(1H-2-Phenylimidazolylmethyl) phenylsulphonyl-L-leucine ethyl ester,

N-Methyl-N-4-(1H-2-nitroimidazolylmethyl) phenylsulphonyl-L-leucine ethyl ester, N-4-(1H-4,5-Diphenylimidazolylmethyl) phenylsulphonyl-L-leucinyl ethyl ether, N-4-(1H-2-Butyl-4-chloro-5-hydroxymethylimidazolylmethyl)phenylsulphonyl-L-leucine ethyl ester, N-Methyl-N-4-(1H-2-butyl-4-chloro-5-hydroxymethylimidazolymethyl)phenylsulphonyl-L-leucine ethyl ester, N-Methyl-N-4-(1H-2-butyl-4-chloro-5-hydroxymethylimidazolymethyl)phenylsulphonyl-L-leucine n-propyl ester, N-Methyl-N-4-(1H-2-ethylimidazolylmethyl) phenylsulphonyl-L-leucine methyl ester, N-Methyl-N-4-(1H-2-n-propylimidazolylmethyl) phenylsulphonyl-L-leucine methyl ester, N-4-(3H-Imidazo[4,5-b]pyridylmethyl)phenylsulphonyl-L-leucinyl ethyl ether, N-4-(1H-Imidazo[4,5-b]pyridylmethyl)phenylsulphonyl-L-leucinyl ethyl ether, N-Methyl-N-4-(9H-2,6-dichloropurinylmethyl) phenylsulphonyl-L-leucine n-propyl ester, N-4-(1H-Imidazolylmethyl)phenylsulphonyl-L-leucinyl t-butyldiphenylsilyl ether, N-4-(1H-Imidazolylmethyl)phenylsulphonyl-L-leucinol, N-4-(1H-2-Methylimidazolylmethyl)phenylsulphonyl-L-leucinol, N-Methyl-N-4-(1H-2-butyl-4-chloro-5-hydroxymethylimidazolylmethyl)phenylsulphonyl-L-leucine, N-Methyl-N-4-(1H-2-ethylimidazolylmethyl) phenylsulphonyl-L-leucine, N-Methyl-N-4-(1H-2-n-propylimidazolylmethyl) phenylsulphonyl-L-leucine, or a salt of such a compound.

12. A method for the treatment of diseases or physiological conditions of humans or mammalian animals mediated by platelet activating factor, comprising administering to the patient an amount of any of the compounds claimed in claims 1, 9, 10, or 11, effective to antagonize the effects of platelet activating factor on target cells responsible for such diseases or physiological conditions.

13. The method of claim 12, comprising administering the compound together with a pharmaceutically or veterinarily acceptable carrier.

14. A method for the treatment of diseases or physiological conditions of humans or mammalian animals mediated by angiotensin II, comprising administering to the patient an amount of any of the compounds claimed in claims 1, 9, 10 or 11, effective to antagonize the effects of angiotensin II on target cells responsible for such diseases or physiological conditions.

15. The method of claim 14, comprising administering the compound together with a pharmaceutically or veterinarily acceptable carrier.

* * * * *